(12) United States Patent
Kubota et al.

(10) Patent No.: US 11,170,921 B2
(45) Date of Patent: Nov. 9, 2021

(54) MARKER COIL AND MARKER COIL UNIT

(71) Applicants: Hiroshi Kubota, Ishikawa (JP); Yasuyuki Kawabuchi, Ishikawa (JP)

(72) Inventors: Hiroshi Kubota, Ishikawa (JP); Yasuyuki Kawabuchi, Ishikawa (JP)

(73) Assignee: Ricoh Company, Ltd., Tokyo (JP)

( * ) Notice: Subject to any disclaimer, the term of this patent is extended or adjusted under 35 U.S.C. 154(b) by 388 days.

(21) Appl. No.: 15/608,037

(22) Filed: May 30, 2017

(65) Prior Publication Data
US 2017/0352457 A1   Dec. 7, 2017

(30) Foreign Application Priority Data

Jun. 7, 2016  (JP) .............................. JP2016-113339
Apr. 24, 2017  (JP) .............................. JP2017-085161

(51) Int. Cl.
| | |
|---|---|
| *A61B 5/00* | (2006.01) |
| *A61B 90/00* | (2016.01) |
| *H01F 5/00* | (2006.01) |
| *H01F 5/04* | (2006.01) |
| *A61B 5/245* | (2021.01) |

(Continued)

(52) U.S. Cl.
CPC ............. *H01F 5/003* (2013.01); *A61B 5/245* (2021.01); *A61B 5/6803* (2013.01); *H01F 5/04* (2013.01); *A61B 5/369* (2021.01); *A61B 2090/3958* (2016.02); *A61B 2090/3991* (2016.02); *A61B 2562/0223* (2013.01); *H01F 38/14* (2013.01)

(58) Field of Classification Search
CPC .............. A61B 5/04008; A61B 5/0223; A61B 5/0467–0484; A61B 5/6803; A61B 2034/2051; A61B 2034/2072; A61B 2090/3983; A61B 2090/3954–3958; A61B 2090/397–3975; H01F 5/00; H01F 5/003; H01F 5/04; H01F 27/303; H01F 27/2804
See application file for complete search history.

(56) References Cited

U.S. PATENT DOCUMENTS 5,584,838 A * 12/1996 Rona .................. A61B 17/1707
                                                            324/226
5,706,811 A *  1/1998 Takeda ................ A61B 5/0555
                                                            600/414

(Continued)

FOREIGN PATENT DOCUMENTS

| JP | S61-010897 U | 1/1986 |
| JP | 2002-253531  | 9/2002 |

(Continued)

OTHER PUBLICATIONS

Electrical Engineering Dictionary. Ed. Phillip A. Laplante. Boca Raton: CRC Press LLC, 2000, p. 541. (Year: 2000).*

(Continued)

*Primary Examiner* — Angela M Hoffa
(74) *Attorney, Agent, or Firm* — IPUSA, PLLC

(57) ABSTRACT

A marker coil includes a flexible substrate, a coil formed on the substrate by wiring, and a substrate holding part that is capable of being attached to a testee. A convex shape is formed in one of the substrate and the substrate holding part, and an engaging part for engaging the convex shape is formed in the other one of the substrate and the substrate holding part.

11 Claims, 22 Drawing Sheets

(51) Int. Cl.
*H01F 38/14* (2006.01)
*A61B 5/369* (2021.01)

(56) References Cited

U.S. PATENT DOCUMENTS

| | | | | |
|---|---|---|---|---|
| 6,381,481 | B1* | 4/2002 | Levendowski | A61B 5/0478 |
| | | | | 600/383 |
| 8,195,272 | B2* | 6/2012 | Piferi | G01R 33/34007 |
| | | | | 128/845 |
| 8,907,667 | B2* | 12/2014 | Klein | G01R 33/04 |
| | | | | 324/244 |
| 8,989,835 | B2* | 3/2015 | Badower | A61B 5/165 |
| | | | | 600/383 |
| 9,095,266 | B1* | 8/2015 | Fu | A61B 5/0476 |
| 2013/0057270 | A1* | 3/2013 | Klein | G01R 33/04 |
| | | | | 324/244 |
| 2013/0324786 | A1 | 12/2013 | Rogachefsky | |
| 2014/0051044 | A1* | 2/2014 | Badower | A61B 5/165 |
| | | | | 434/236 |
| 2015/0327813 | A1* | 11/2015 | Fu | A61B 5/0476 |
| | | | | 600/383 |
| 2016/0174862 | A1* | 6/2016 | Yu | A61B 5/0522 |
| | | | | 600/409 |
| 2016/0223622 | A1* | 8/2016 | Yu | G01R 33/035 |
| 2017/0352457 | A1* | 12/2017 | Kubota | H01F 5/003 |
| 2018/0211754 | A1* | 7/2018 | Hattori | H01F 17/0013 |
| 2018/0338697 | A1* | 11/2018 | Sackellares | A61B 5/04026 |

FOREIGN PATENT DOCUMENTS

| | | | | |
|---|---|---|---|---|
| JP | 4029313 | * | 1/2008 | A61B 5/55 |
| JP | 2010-148578 | | 7/2010 | |

OTHER PUBLICATIONS

Office Action dated Feb. 9, 2021 issued with respect to the corresponding Japanese Patent Application No. 2017-085161.

* cited by examiner

MARKER COIL AND MARKER COIL UNIT

BACKGROUND OF THE INVENTION

1. Field of the Invention

The present disclosure relates to a marker coil and marker coil unit.

2. Description of the Related Art

A magnetoencephalograph is a device for measuring weak magnetic field generated by an electrical activity of a brain by a superconducting quantum interference device (SQUID) sensor array and identifying a position of a main neural activity from a relation between a magnetic field source and a magnetic field distribution. The magnetoencephalograph is often used, for example, for identifying an epileptic focal point in a clinical aspect and for measuring a time-dependent variation of a brain activity in a research field.

The magnetoencephalograph can measure a magnetic field. However, with the magnetoencephalograph, an image of a brain is not obtained. Consequently, it may not be possible to identify from which part of the brain the magnetic field measured by the magnetoencephalograph is generated.

Thus, prior to measuring a magnetic field generated in a head by the magnetoencephalograph, a marker coil for the magnetoencephalograph is attached to the head of a testee. In a state in which the head is fixed, a weak alternating current is caused to flow in the marker coil for the magnetoencephalograph, and the position is measured by the magnetoencephalograph.

Furthermore, a marker for a magnetic resonance diagnosing apparatus (Magnetic Resonance Imaging: MRI) (a MRI marker) is attached to a position that is the same as the position of the marker coil for the magnetoencephalograph on the head of the testee, and, in a state in which the head is fixed, an image of the brain is captured by the MRI. The image captured by the MRI includes a real image of the MRI marker.

By matching the position of the marker coil for the magnetoencephalograph with the position of the MRI marker, a coordinate system of the magnetoencephalograph can be matched with a coordinate system of the MRI. Coordinates of an activity position estimated by the magnetoencephalograph can be superimposed on the image of the brain measured by the MRI to be used.

As the marker coil used for the above-described superposition, for example, a structure has been proposed such that, on both surfaces of a print board in which a hole for identifying a position is formed, respective spiral print coils centered on the hole for identifying the position are formed, and the respective print coils formed on the both surfaces of the print board are serially connected. For this marker coil for the magnetoencephalograph, the print board is accommodated in a housing (casing) (cf. Patent Document 1 (Japanese Patent No. 4029313), for example).

SUMMARY OF THE INVENTION

The marker coil itself is heavy and it takes a long time to attach the marker coil, so that the above-described marker coil may provide an unpleasant feeling to a testee. Thus, it is difficult to attach the above-described marker coil to an infant (less than one year in age) and a little child (greater than or equal to one year and less than or equal to six years in age).

There is a need for a marker coil that can be easily attached to an infant and a little child.

According to an aspect of the present disclosure, there is provided a marker coil including a flexible substrate, a coil formed on the substrate by wiring, and a substrate holding part that is capable of being attached to a testee, wherein a convex shape is formed in one of the substrate and the substrate holding part, and wherein an engaging part for engaging the convex shape is formed in the other one of the substrate and the substrate holding part.

According to another aspect of the present disclosure, there is provided a marker coil unit including a marker coil including a flexible substrate, a coil formed on the substrate by wiring, and a substrate holding part that is capable of being attached to a testee, wherein a convex shape is formed in one of the substrate and the substrate holding part, and an engaging part for engaging the convex shape is formed in the other one of the substrate and the substrate holding part; and an electric current input part configured to input an electric current to the coil, wherein the electric current input part includes a connector formed on the substrate and a wire for coupling a terminal of the connector with the coil.

According to another aspect of the present disclosure, there is provided a marker coil including a flexible substrate, and a plurality of coils, each of the plurality of coils being formed on the substrate by wiring, wherein the marker coil is capable of being attached to a part of a body of a testee in a headband shape.

According to another aspect of the present disclosure, there is provided a marker coil unit including a marker coil including a flexible substrate, and a plurality of coils, each of the plurality of coils being formed on the substrate by wiring, wherein the marker coil is capable of being attached to a part of a body of a testee in a headband shape, and an electric current input part configured to input an electric current to the coil, wherein the electric current input part includes a connector formed on the substrate and a wire for coupling a terminal of the connector with the coil.

According to the disclosed technology, a marker coil can be provided that can be easily attached to an infant and a little child.

Other objects, features and advantages of the present invention will become more apparent from the following detailed description when read in conjunction with the accompanying drawings.

DETAILED DESCRIPTION OF THE PREFERRED EMBODIMENTS

Figure 1:
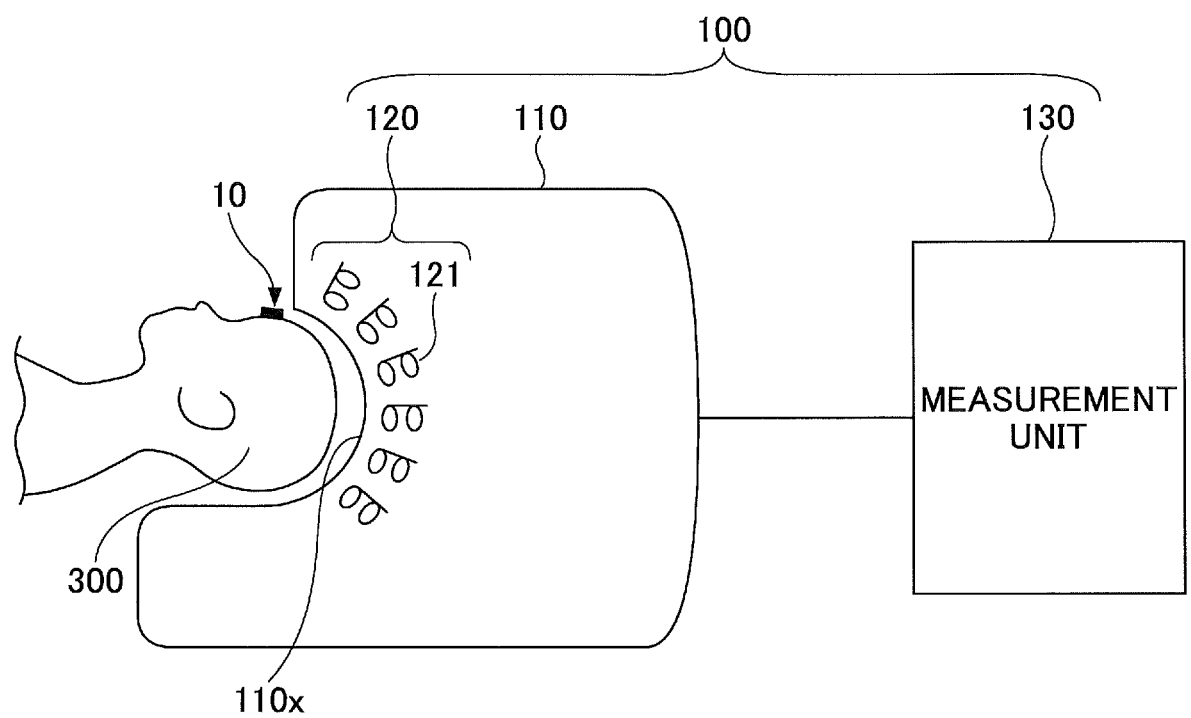
FIG. 1 is a diagram illustrating an outline of magnetoencephalograph.

In the following, an embodiment is described by referring to the drawings. In the drawings, the same reference numerals may be attached to identical components, and duplicate descriptions may be omitted.

(Magnetoencephalograph)

FIG. 1 is a diagram illustrating an overview of a magnetoencephalograph. The magnetoencephalograph 100 includes a dewar 110; a SQUID sensor array 120; and a measurement unit 130.

The dewar 110 reserves liquid helium required for a cryogenic operation of the SQUID sensor array 120. In the dewar 110, a recess 110x is formed, into which a part of a head 300 of a testee is to be inserted.

The SQUID sensor array 120 includes a plurality of SQUID sensors 121 (e.g., approximately one hundred sixty SQUID sensors 121) arranged in the dewar 110. Each SQUID sensor 121 is oriented in a direction in which a weak magnetic field generated by neural activity of a brain can be measured on a scalp.

The measurement unit 130 measures strength of the magnetic field detected by each SQUID sensor 121, and the measurement unit 130 generates magnetic field distribution data indicating intensity distribution of the magnetic field generated by the brain. The magnetic field distribution data can be graphically represented, for example, by an isomagnetic diagram.

As described above, the magnetoencephalograph 100 can generate the magnetic field distribution data. However, an image of a brain may not be obtained with the magnetoencephalograph 100, so that it may not be possible to identify the part of the brain at which the magnetic field detected by the magnetoencephalograph 100 is generated.

Thus, prior to measuring a magnetic field generated in the head by the magnetoencephalograph 100, a marker coil unit 10 is attached to the head of a testee. In a state in which the head 300 is fixed, a weak alternating current is caused to flow in the marker coil unit 10, and the position is measured by the measurement unit 130.

The coordinates of positions at which the respective SQUID sensors 121 are arranged are known in advance. Thus, when an electric current is caused to flow in the marker coil unit 10, by detecting, by the measurement unit 130, a position of the SQUID sensor 121 that detects the magnetic field, the position of the marker coil unit 10 can be identified.

After identifying the position of the marker coil unit 10, magnetic field distribution data of the magnetic field generated in the head of the testee is generated by the magnetoencephalograph 100 while applying visual stimulation, auditory stimulation, electrical stimulation, etc., to the testee. At this time, no electric current is caused to flow in the marker coil unit 10.

Separately from the generation of the magnetic field distribution data by the magnetoencephalograph 100, a MRI marker is attached to the same position of the marker coil unit 10 on the head of the testee, and a three-dimensional tomographic image of the brain is captured by the MRI. The three-dimensional tomographic image captured by the MRI includes a real image of the MRI marker. By matching the position of the marker coil unit 10 with the position of the MRI marker, a coordinate system of the magnetoencephalograph 100 can be matched with a coordinate system of the MRI. Namely, coordinates of an activity position estimated by the magnetoencephalograph 100 can be superimposed on the three-dimensional tomographic image of the brain measured by the MRI to be used.

(Marker Coil Unit)

Figure 2A:
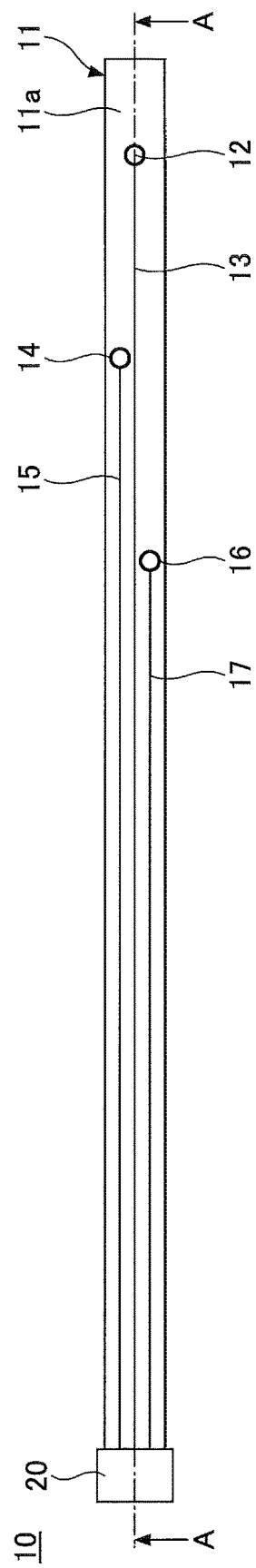
FIGS. 2A through 2C are diagrams exemplifying a marker coil according to an embodiment.
Figure 2B:
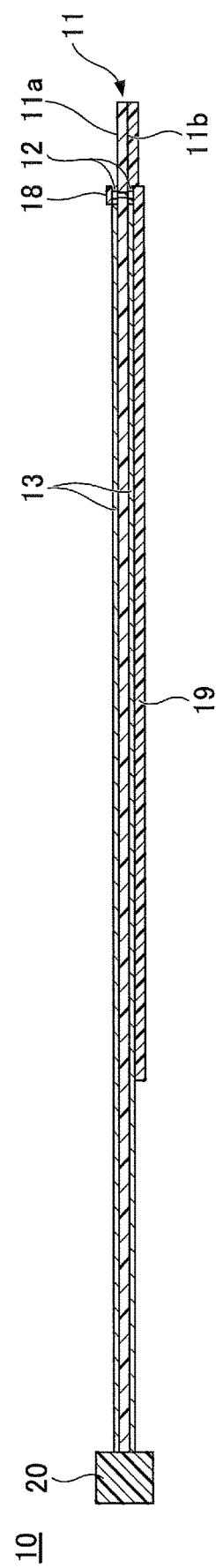
Figure 2C:
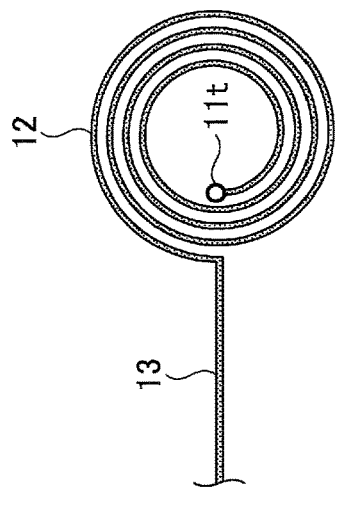

FIG. 2 is a diagram exemplifying the marker coil unit according to the embodiment. FIG. 2A is a plan view. FIG. 2B is a cross-sectional view along the line A-A in FIG. 2A. FIG. 2C is a plan view in which a part of the marker coil unit in the vicinity of the coil 12 is enlarged. However, in FIG. 2A, depiction of a reinforcing plate 18 is omitted, and in FIG. 2B, the depiction of the cross section of the coil 12 is simplified.

As illustrated in FIG. 2, the marker coil unit 10 includes a substrate 11; a coil 12; wiring 13; a coil 14; wiring 15; a coil 16; wiring 17; the reinforcing plate 18; an anti-slip sheet 19; and a connector 20.

In the marker coil unit 10, the substrate 11, the coil 12, the coil 14, the coil 16, the reinforcing plate 18, and the anti-slip sheet 19 form marker coils. In other words, the component formed by adding the wiring 13, the wiring 15, the wiring 17, and the connector 20, which form an electric current input part, to the marker coils is the marker coil unit 10.

The weight of the marker coil unit 10 can be adjusted to be approximately less than or equal to 30 g, for example. The marker coil unit 10 is designed, so that it can be easily attached to an infant. However, the marker coil unit 10 may be attached to a little child, a junior high school student, a high school student, an adult, etc.

As the substrate 11, an elongated flexible printed wiring board (FPC: Flexible Printed Circuits) formed of flexible polyimide may be used. As the size of the substrate 11, the length in the longitudinal direction may be approximately 450 mm and the length in the width direction may be approximately 30 mm, for example. The width of the substrate 11 may be approximately in a range from 10 μm to 100 μm, for example.

The coil 12 is a printed coil formed by wiring. The coil 12 has a structure such that a spiral pattern formed on one surface 11a of the substrate 11 and a spiral pattern formed on the other surface 11b are serially coupled by through wiring lit that passes through the substrate 11.

In the coil 12, the spiral pattern formed on the one surface 11a of the substrate 11 and the spiral pattern formed on the other surface 11b are formed at positions that approximately overlap in a plan view. Here, the plan view means that an object is observed in a normal direction of the one surface 11a or the other surface 11b of the substrate 11.

The wiring 13 is formed of a pattern formed on the one surface 11a of the substrate 11 and a pattern formed on the other surface 11b. In the wiring 13, the pattern formed on the one surface 11a of the substrate 11 and the pattern formed on the other surface 11b are formed at positions that approximately overlap in the plan view.

In the wiring 13, the pattern formed on the one surface 11a of the substrate 11 forms coupling between one of terminals of the connector 20 and one end of the spiral pattern formed on the one surface 11a of the substrate 11. Additionally, the pattern formed on the other surface 11b of the substrate 11 forms coupling between another one of the terminals of the connector 20 and one end of the spiral pattern formed on the other surface 11b of the substrate 11 of the coil 12.

When an electric current is supplied from the terminal of the connector 20 to the coil 12 through the wiring 13, electric currents in the same phases flow in the spiral pattern formed on the one surface 11a of the substrate 11 of the coil 12 and in the spiral pattern formed on the other surface 11b, respectively. In contrast, electric currents in respective phases that are opposite each other flow in the pattern of the wiring 13 formed on the one surface 11a of the substrate 11 and in the other pattern of the wiring 13 formed on the other surface 11b, respectively.

With this structure, when an electric current flows in the wiring 13 and the coil 12, a magnetic field can be generated only in the coil 12 without generating a magnetic field in the wiring 13. Note that the coils 14 and 16 have the same structures as the structure of the coil 12, and the wiring 15 and the wiring 17 have the same structures as the structure of the wiring 13.

On one side of each of the coils 12, 14, and 16, the reinforcing plate 18 is formed. The reinforcing plate 18 is formed so as to prevent, when the marker coil unit 10 is attached to the head of the testee, an error for estimating the position from being increased due to distortion in each coil. The reinforcing plate 18 may be formed at both sides of the coils 12, 14, and 16.

For example, the reinforcing plate 18 may be formed of a resin, such as acrylic. A planar shape of the reinforcing plate 18 may be, for example, a circular shape. However, the planar shape of the reinforcing plate 18 is not limited to the circular shape. Here, the planar shape is defined to be a shape of an object when the object is observed in a normal direction of the one surface 11a or the other surface 11b of the substrate 11.

The anti-slip sheet 19 is for increasing frictional force between the marker coil unit and the testee, so that, when the marker coil unit 10 is attached to the testee, a positional shift can be prevented from occurring. As the anti-slip sheet 19, for example, a urethane resin may be used.

The connector 20 is formed at one end side of the substrate 11. The connector 20 is a part that is coupled to an electric current supply device (such as an oscillator) for supplying electric currents to the respective coils 12, 14, and 16 of the marker coil unit 10. The electric current supply device may be provided in the measurement unit 130 of the magnetoencephalograph 100, or the electric current supply device may be provided separately from the measurement unit 130.

As the connector 20, a modular jack may be used, for example. By providing the connector 20, the marker coil unit 10 can be collectively coupled to the electric current supply device, so that establishment of the coupling between the electric current supply device and the marker coil unit 10 can be facilitated. In this case, the electric current input parts for supplying electric current to the coils 12, 14, and 16 are formed of the connector 20 and the wiring 13, the connector 20 and the wiring 15, and the connector 20 and the wiring 17, respectively. Here, the wiring 13 is for coupling a terminal of the connector 20 with the coil 12. The wiring 15 is for coupling a terminal of the connector 20 with the coil 14. The wiring 17 is for coupling a terminal of the connector 20 with the coil 16.

However, the connector 20 may not be used. For example, a terminal to be connected to the wiring 13 may be exposed at one end side of the substrate 11, and the exposed terminal may be nipped by a clip connected to the electric current supply device. In this case, the electric current input part for supplying an electric current to the coil 12 is formed of the corresponding terminal exposed at the one end side of the substrate 11 and the wiring 13. The electric current input part for supplying an electric current to the coil 14 is formed of the corresponding terminal exposed at the one end side of the substrate 11 and the wiring 15. The electric current input part for supplying an electric current to the coil 16 is formed of the corresponding terminal exposed at the one end side of the substrate 11 and the wiring 17.

Figure 3:
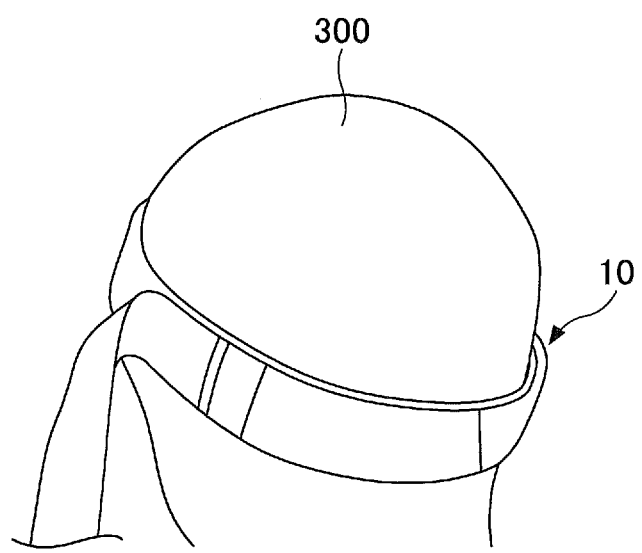
FIG. 3 is a diagram exemplifying a situation where the marker coil according to the embodiment is attached to a head of a testee.

FIG. 3 is a diagram exemplifying a situation in which the marker coil unit 10 according to the embodiment is attached to a head of a testee. Here, a mannequin is used while assuming that the testee is an infant. As shown in FIG. 3, the marker coil unit 10 is attached to the head 300 in a headband shape while arranging the anti-slip sheet 19 to face the head 300. A part of the marker coil unit 10 that overlaps the marker coil unit 10 itself by going around the head 300 once may be secured by a double sided tape, for example.

Note that, in order to determine the coordinate system in x, y, and z directions of the magnetoencephalograph 100, it is necessary to provide three or more coils in the marker coil unit 10. In FIG. 1, the example is shown in which three coils are formed in the marker coil unit 10. However, four or more coils may be formed.

In this manner, in the marker coil unit 10, the weight is reduced by forming the coils 12, 14, and 16 on the flexible substrate 11 by wiring. In addition, by forming the substrate 11 to have the elongated shape, so that the marker coil unit 10 can be attached to the head of the testee in the headband shape, the marker coil unit 10 can be attached to the testee with a simplified operation. Consequently, unpleasant feeling for the testee can be mitigated, so that the marker coil unit 10 can be easily attached to an infant or a little child.

Additionally, in the marker coil unit 10, the substrate 11 is formed to have the elongated shape so as to be able to be attached to the head of the testee in the headband shape, so that the marker coil unit 10 can be easily attached to a hairy part of the head.

Furthermore, in the marker coil unit 10, the double sided tape does not touch the skin of the testee, so that itchiness of the skin of the testee can be prevented from occurring. The marker coil unit 10 is particularly suitable for attaching to an infant sensitive to itching.

Figure 4A:
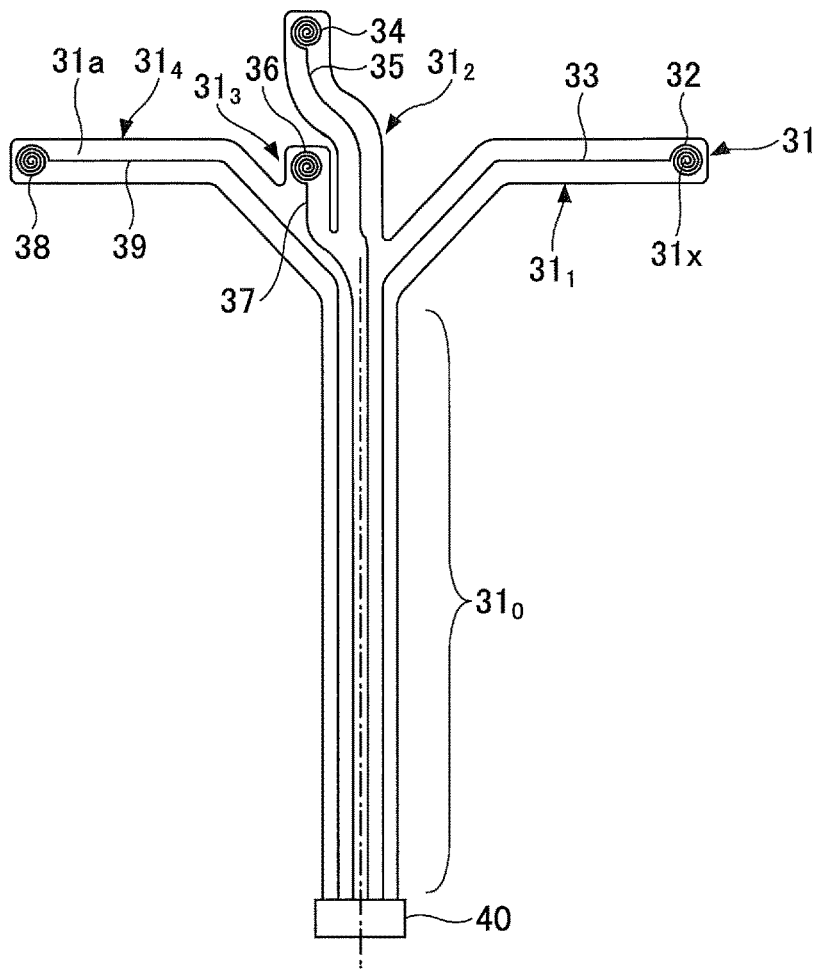
FIGS. 4A through 4C are plan views exemplifying a part of the marker coil according to an embodiment excluding a coil holding part.
Figure 4B:
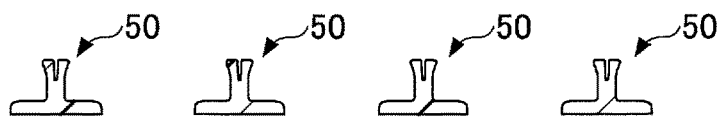
Figure 4C:
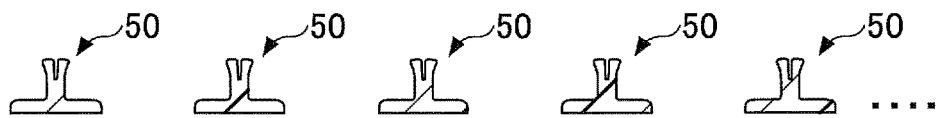

FIG. 4 is a diagram exemplifying a marker coil unit 30 according to another embodiment. FIG. 4A is a plan view exemplifying a part of the marker coil unit 30 excluding substrate holding parts 50. FIGS. 4B and 4C are cross-sectional views exemplifying the substrate holding parts 50 of the marker coil unit 30.

Figure 5A:
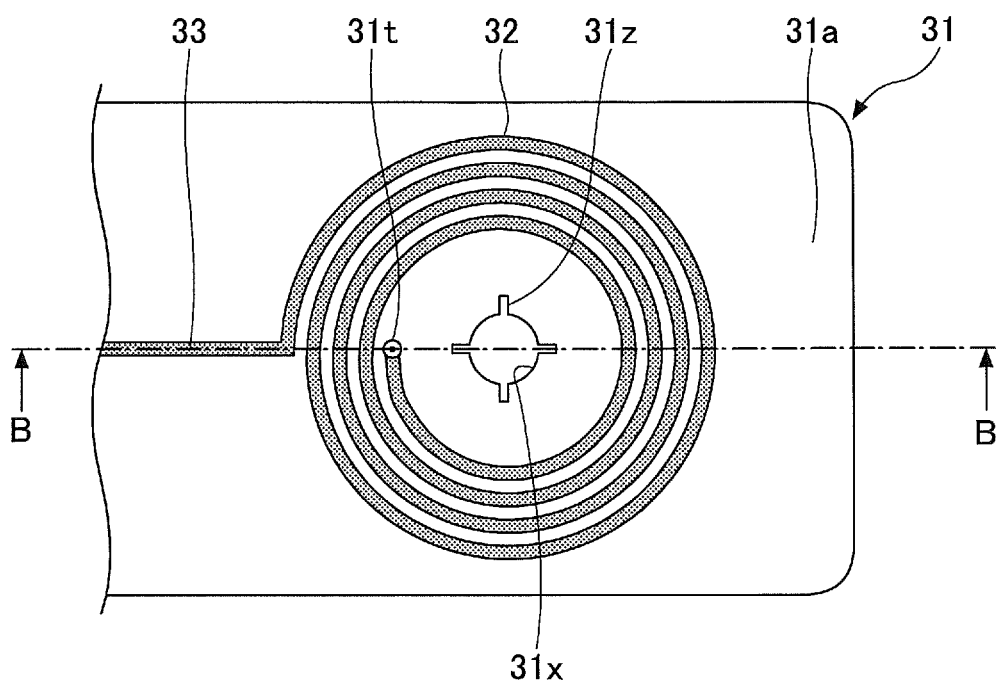
FIGS. 5A and 5B are partial enlarged views exemplifying a vicinity of a coil of the marker coil according to the embodiment.
Figure 5B:
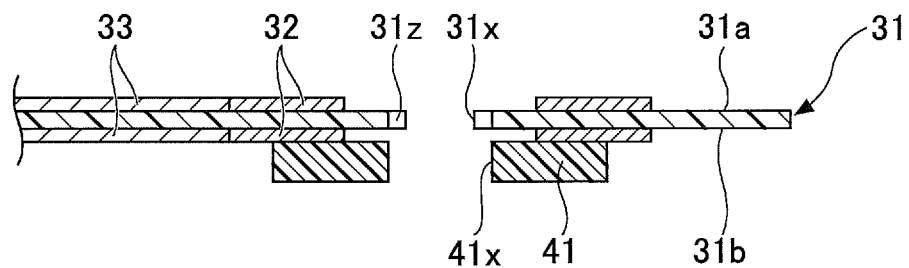
Figure 6A:
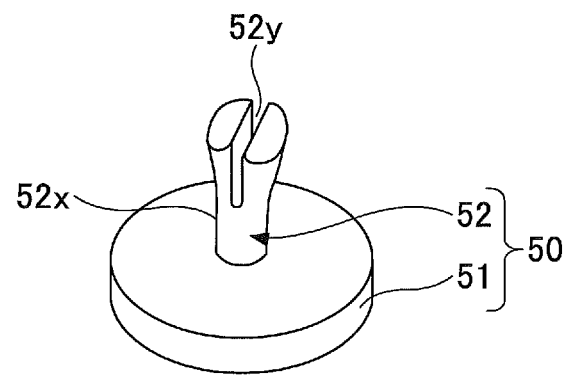
FIGS. 6A and 6B are diagrams exemplifying the coil holding part of the marker coil according to the embodiment.
Figure 6B:
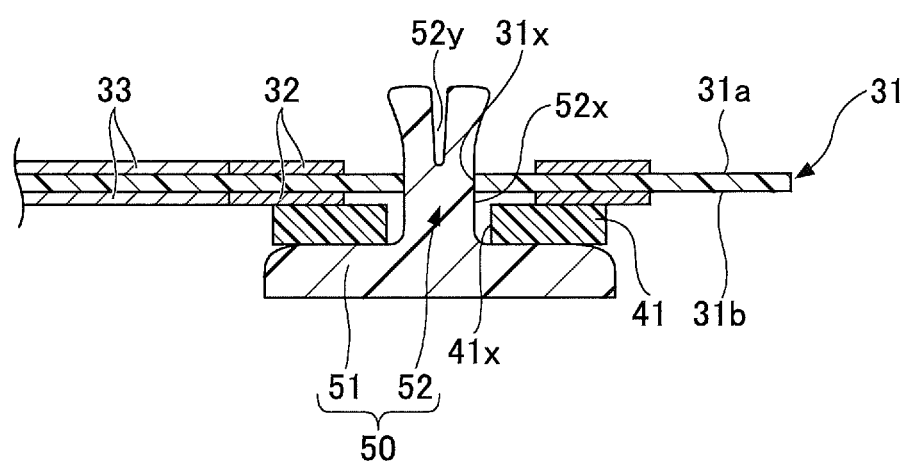

FIG. 5 is a partial enlarged view exemplifying a vicinity of the coil of the marker coil unit 30 according to the embodiment. FIG. 5A is a plan view. FIG. 5B is a cross-sectional view along the line B-B in FIG. 5A. However, in FIG. 5B, the cross section of the coil 32 is simplified. FIG. 6 is a diagram exemplifying the substrate holding part 50 of the marker coil unit 30 according to the embodiment. FIG. 6A is a perspective view of the substrate holding part 50. FIG. 6B is a cross-sectional view illustrating a situation in which the substrate holding part 50 is attached to the substrate.

As illustrated in FIG. 4 through FIG. 6, the marker coil unit 30 includes a substrate 31; a coil 32; wiring 33; a coil 34, wiring 35; a coil 36; wiring 37; a coil 38; wiring 39; a connector 40; a reinforcing plate 41; and the substrate holding parts 50. Note that, in the marker coil unit 30, the substrate holding parts 50 and the other part are formed as separate components. When the marker coil unit 30 is attached to a head of a testee, the substrate holding parts 50 and the other part are integrated.

One substrate holding part 50 is inserted into a hole 31x at the center side of each of the coils 32, 34, 36, and 38. Thus, as illustrated in FIG. 4B, the number of the substrate holding parts 50 included in the marker coil unit 30 is the same as the number of the coils (four in the embodiment). However, considering loss of breakage of the substrate holding parts 50, as illustrated in FIG. 4C, the number of the substrate holding parts 50 included in the marker coil unit 30 may be greater than or equal to the number of the coils.

In the marker coil unit 30, the substrate 31, the coil 32, the coil 34, the coil 36, the coil 38, the reinforcing plate 41, and the substrate holding parts 50 form the marker coils. In other words, the marker coil unit 30 is formed by adding the wiring 33, the wiring 35, the wiring 37, the wiring 39, and the connector 40, which form an electric current input part, to the marker coils.

The weight of the marker coil unit 30 (including the weight of the substrate holding parts 50) can be adjusted, for example, to be approximately less than or equal to 20 g. The marker coil unit 30 is designed, so that it can be easily attached to a little child. However, the marker coil unit 30 may be attached to an infant, a junior high school student, a high school student, an adult, etc.

As the substrate 31, a flexible printed wiring board formed of flexible polyimide may be used. The width of the substrate 31 may be approximately in a range from 10 μm to 100 μm, for example. The substrate 31 includes a common part $31_0$ connected to the connector 40; and coil forming parts $31_1$, $31_2$, $31_3$, and $31_4$, which are branched from the common part $31_0$.

The coil 32 is formed in the coil forming part $31_1$. The coil 32 has a structure such that a spiral pattern formed on one surface 31a of the substrate 31 and a spiral pattern formed on the other surface 31b are serially coupled by through wiring 31t that passes through the substrate 31. In the coil 32, the spiral pattern formed on the one surface 31a of the substrate 31 and the spiral pattern formed on the other surface 31b are formed at positions that approximately overlap in a plan view. At the center side of the coil 32 of the substrate 31, a hole 31x having an approximate circular shape is formed.

In the coil forming part $31_1$ and the common part $31_0$, the wiring 33 is formed of a pattern formed on the one surface 31a of the substrate 31 and a pattern formed on the other surface 31b. In the wiring 33, the pattern formed on the one surface 31a of the substrate 31 and the pattern formed on the other surface 31b are formed at positions that approximately overlap in the plan view.

In the wiring 33, the pattern formed on the one surface 31a of the substrate 31 forms coupling between one of terminals of the connector 40 and one end of the spiral pattern formed on the one surface 31a of the substrate 31 of the coil 32. Additionally, the pattern formed on the other surface 31b of the substrate 31 forms coupling between another one of the terminals of the connector 40 and one end of the spiral pattern formed on the other surface 31b of the substrate 31 of the coil 32.

The coil 34 is formed in the coil forming part $31_2$. The coil 34 has a structure that is the same as the structure of the coil 32. At the center side of the coil 34 of the substrate 31, a hole 31x having an approximate circular shape is formed.

In the coil forming part $31_2$ and the common part $31_0$, the wiring 35 is formed of a pattern formed on the one surface 31a of the substrate 31 and a pattern formed on the other surface 31b. In the wiring 35, the pattern formed on the one surface 31a of the substrate 31 and the pattern formed on the other surface 31b are formed at positions that approximately overlap in the plan view.

In the wiring 35, the pattern formed on the one surface 31a of the substrate 31 forms coupling between one of terminals of the connector 40 and one end of the spiral pattern formed on the one surface 31a of the substrate 31 of the coil 34. Additionally, the pattern formed on the other surface 31b of the substrate 31 forms coupling between another one of the terminals of the connector 40 and one end of the spiral pattern formed on the other surface 31b of the substrate 31 of the coil 34.

The coil 36 is formed in the coil forming part $31_3$. The coil 36 has a structure that is the same as the structure of the coil 32. At the center side of the coil 36 of the substrate 31, a hole 31x having an approximate circular shape is formed.

In the coil forming part $31_3$ and the common part $31_0$, the wiring 37 is formed of a pattern formed on the one surface 31a of the substrate 31 and a pattern formed on the other surface 31b. In the wiring 37, the pattern formed on the one surface 31a of the substrate 31 and the pattern formed on the other surface 31b are formed at positions that approximately overlap in the plan view.

In the wiring 37, the pattern formed on the one surface 31a of the substrate 31 forms coupling between one of terminals of the connector 40 and one end of the spiral pattern formed on the one surface 31a of the substrate 31 of the coil 36. Additionally, the pattern formed on the other surface 31b of the substrate 31 forms coupling between another one of the terminals of the connector 40 and one end of the spiral pattern formed on the other surface 31b of the substrate 31 of the coil 36.

The coil 38 is formed in the coil forming part $31_4$. The coil 38 has a structure that is the same as the structure of the coil 32. At the center side of the coil 38 of the substrate 31, a hole 31x having an approximate circular shape is formed.

In the coil forming part $31_4$ and the common part $31_0$, the wiring 39 is formed of a pattern formed on the one surface 31a of the substrate 31 and a pattern formed on the other surface 31b. In the wiring 39, the pattern formed on the one surface 31a of the substrate 31 and the pattern formed on the other surface 31b are formed at positions that approximately overlap in the plan view.

In the wiring 39, the pattern formed on the one surface 31a of the substrate 31 forms coupling between one of terminals of the connector 40 and one end of the spiral pattern formed on the one surface 31a of the substrate 31 of the coil 38. Additionally, the pattern formed on the other surface 31b of the substrate 31 forms coupling between another one of the terminals of the connector 40 and one end of the spiral pattern formed on the other surface 31b of the substrate 31 of the coil 38.

When an electric current is supplied from the terminal of the connector 40 to the coil 32 through the wiring 33, electric currents in the same phases flow in the spiral pattern formed on the one surface 31a of the substrate 31 of the coil 32 and in the spiral pattern formed on the other surface 31b, respectively. In contrast, electric currents in respective phases that are opposite each other flow in the pattern of the wiring 33 formed on the one surface 31a of the substrate 31 and in the other pattern of the wiring 33 formed on the other surface 31b, respectively.

With this structure, when an electric current flows in the wiring 33 and the coil 32, a magnetic field can be generated only in the coil 32 without generating a magnetic field in the wiring 33. Note that the same applies to the wiring 35 and the coil 34, the wiring 37 and the coil 36, and the wiring 39 and the coil 38.

On the other surface 31b of the substrate 31 of the coils 32, 34, 36, and 38, the reinforcing plate 41 is formed. The reinforcing plate 41 is formed so as to prevent, when the marker coil unit 30 is attached to the head of the testee, an error for estimating the position from being increased due to distortion in each coil. The reinforcing plate 41 may be formed at both sides of the coils 32, 34, 36, and 38.

For example, the reinforcing plate 41 may be formed of a resin, such as acrylic. A planar shape of the reinforcing plate 41 may be, for example, a circular shape. However, the planar shape of the reinforcing plate 41 is not limited to the circular shape. At a central portion of the reinforcing plate 41, a hole 41x having an approximate circular shape is formed. The hole 41x of the reinforcing plate 41 is formed approximately coaxially with the hole 31x of the substrate 31. However, the hole 41x is formed, so that a diameter of the hole 41x is greater than a diameter of the hole 31x.

Furthermore, the diameter of the hole 41x of the reinforcing member 41 is preferably greater than or approximately equal to the diameter of a protrusion 52 at a part at which the width of the protrusion 52 becomes a maximum.

The substrate holding part 50 includes a base part 51; and the protrusion 52. In the substrate holding part 50, the protrusion 52 is formed at one side of the base part 51. For example, a double sided tape is attached to the other side of the base part 51, so that the base holding part 50 can be attached to the head of the testee. Note that, in the embodiment, the base part 51 has an approximately disc shape. However the shape of the base part 51 is not limited to this. The base part 51 may have any shape suitable for a part to which the substrate holding part 50 is to be attached.

The substrate holding part 50 is formed of, for example, a resin, such as acrylic, so that the weight of the substrate holding part 50 is extremely light (approximately less than 1 g). Consequently, even if the substrate holding part 50 is attached to the head of the testee, it is unlikely that the testee holds unpleasant feeling.

Weight of a usual marker coil is heavy. Thus, by the weight of the usual marker coil, the measuring position may be deviated from the original position, and the hair may be pulled by the weight of the usual marker coil. However, the weight of the marker coil unit 30 including the substrate holding parts 50 is lighter than the weight of the usual marker coil. Thus, even if the substrate holding part 50 is attached to the hair and the substrate 31 is attached on the substrate holding part, the measuring position may not deviated from the original position by the weight of the marker coil unit 30, and the hair may not be pulled by the weight of the marker coil unit 30. As a result, measurement can be performed at the originally secured position.

After attaching the other side of the base part 51 of the substrate holding part 50 to the head of the testee, by fitting (engaging) the protrusion 52 in the hole 31x of the substrate 31, the substrate holding part 50 holds the substrate 31, and each coil can be arranged at a predetermined position on the head of the testee.

The protrusion 52 of the substrate holding part 50 may have any shape or any size that can be inserted into and removed from the hole 31x of the substrate 31. However, the protrusion 52 may preferably include a narrowed part 52x at the side close to the base part 51. The narrowed part 52x is the part of the protrusion 52 close to the base part 51 such that the diameter of the part is smaller than a diameter of a part of the protrusion 52 separated from the base part 51. The diameter of the narrowed part 52x is adjusted to be slightly smaller than the diameter of the hole 31x of the substrate 31. When the narrowed part 52x of the protrusion 52 is fitted into the hole 31x of the substrate 31, the part of the protrusion 52 above the narrowed part 52x functions as a stopper, so that the protrusion 52 is not easily released from the hole 31x of the substrate 31.

A total thickness obtained by adding the thickness of the reinforcing plate 41, the thickness of the substrate 31, and the thickness of the spiral pattern formed on the other surface 31b of the substrate 31 preferably matches the length of the narrowed part 52x in the axis direction. However, the total thickness is allowed to be slightly greater than or slightly less than the length of the narrowed part 52x in the axis direction. When the total thickness matches the length of the narrowed part 52x in the axis direction, the substrate 31 can be tightly held by the substrate holding part 50.

Additionally, in the protrusion 52, a slit 52y may preferably be formed that divides the protrusion 52 into approximately two equal parts in the axis direction (the direction of the protrusion). When the substrate 31 is to be removed from the substrate holding part 50, the two parts of the protrusion 52 adjacent to the slit 52y move inward, so that the protrusion 52 can be easily removed from the hole 31x of the substrate 31.

Furthermore, one or more notches 31z extending outward from an outer edge of the hole 31x (in the direction toward the coil) may preferably be formed around the hole 31x of the substrate 31. In the example of FIG. 5A, four notches 31z are formed around the hole 31x of the substrate 31. However, the number of the notches 31z is not limited to this. A suitable number of notches 31z may be formed depending on necessity.

By forming the one or more notches 31z, even if the testee accidentally behaves violently and pulls the substrate 31, the substrate 31 can be removed from the substrate holding part 50, and the substrate holding part 50 can be left at the side of the testee. Consequently, the substrate 31 can be attached to the same position again.

Figure 7A:
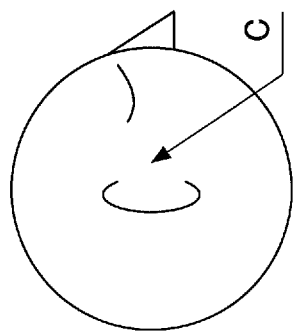
FIGS. 7A through 7C are diagrams illustrating an example of a position at which the coil holding part is arranged.
Figure 7B:
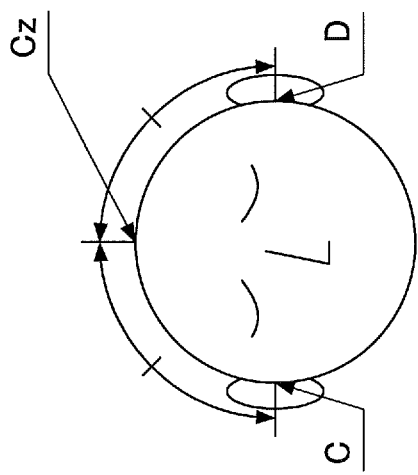
Figure 7C:
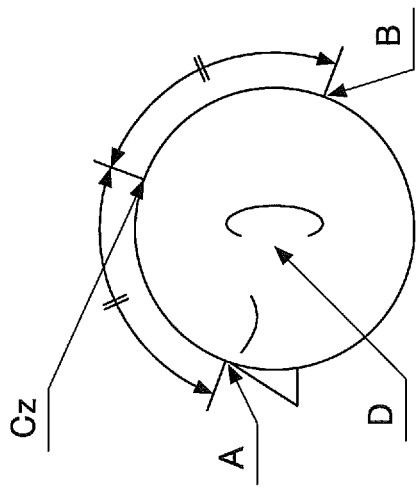

FIG. 7 is a diagram illustrating an example of the positions at which the substrate holding parts 50 are arranged. FIG. 7A is a right side view. FIG. 7B is a front view. FIG. 7C is a left side view.

In the example of FIG. 7, the substrate holding part 50 for holding the coil 36 is attached to Cz according to the EEG 10-20 system. The substrate holding part 50 for holding the coil 34 is attached to a straight line passing through a nasal point A, Cz, and an external occipital protuberance B. The substrate holding part 50 for holding the coil 32 is attached to a straight line passing through a right preauricular point C and Cz. The substrate holding part 50 for holding the coil 38 is attached to a straight line passing through a left preauricular point D and Cz.

Note that the EEG 10-20 system is a method for determining, in the measurement of brain waves, positions at which respective twenty one electrodes in total are to be arranged by dividing the scalp at equal intervals of 10% or 20%. In the EEG 10-20 system, a middle point between a nasal point and an external occipital protuberance is Cz, and a middle point between a right preauricular point and a left preauricular point is Cz.

Figure 8A:
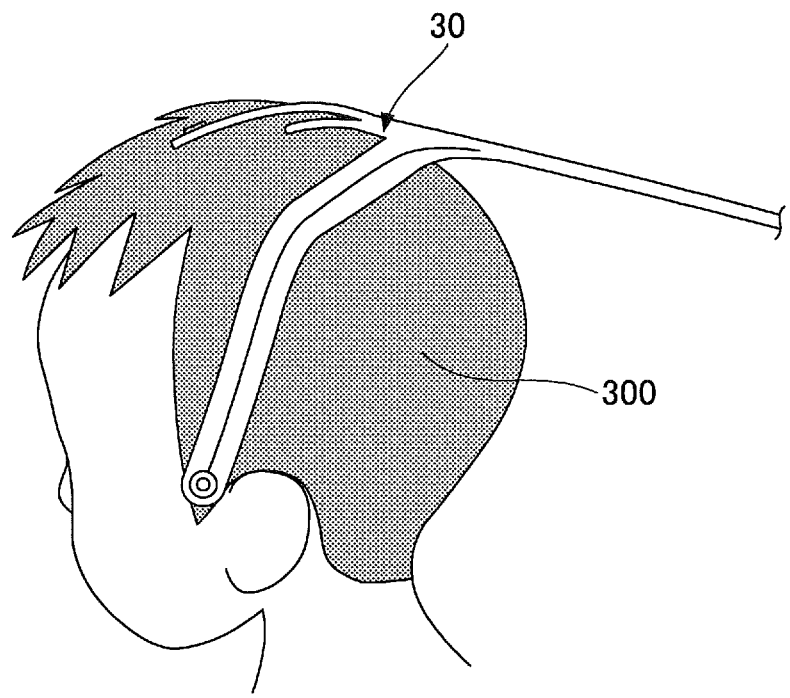
FIGS. 8A and 8B are diagrams exemplifying a situation in which the marker coil according to the embodiment is attached to the head of the testee.
Figure 8B:
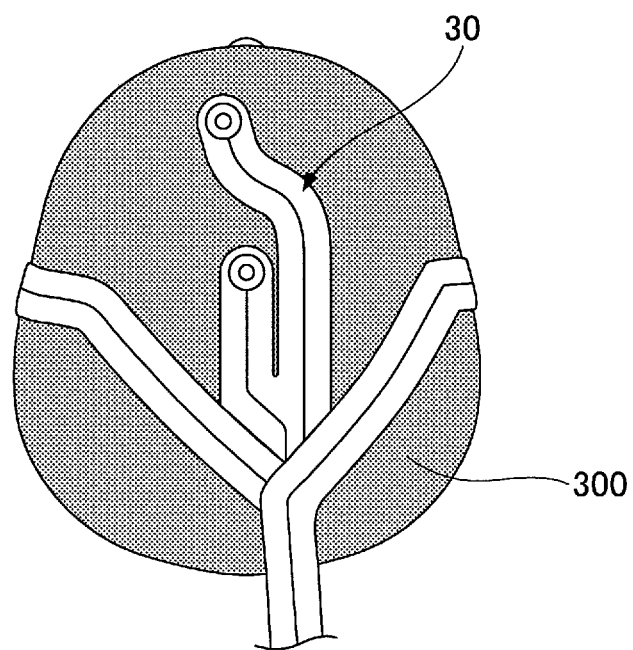

After attaching the substrate holding parts 50 to the respective positions illustrated in FIG. 7, by inserting the protrusions 52 of the substrate holding parts 50 into the center holes 31x of the respective coils, the coils can be held at predetermined positions, as illustrated in FIG. 8, for example. Note that FIG. 8 is a diagram exemplifying a situation in which the marker coil unit 30 according to the embodiment is attached to the head of the testee. FIG. 8A is a left side view. FIG. 8B is a plane view.

Note that, by shifting the line connecting the coil 34 and the coil 36 from the center line in the longitudinal direction of the common part $31_0$ (the one-dot chain line in FIG. 4), when the testee lies down during the examination, as illustrated in FIG. 1, it can be avoided that the weight of the head is applied to the common part $31_0$. Considering the positions illustrated in FIG. 7 to which the coils 34 and 36 are to be attached, respectively, if the center line of the common part $31_0$ in the longitudinal direction is located on a line obtained by extending the line connecting the coil 34 and the coil 36, the common part $31_0$ is held under the occipital region of the head. In this case, when the testee moves the head, the weight of the head is applied to the common part $31_0$, so that the substrate holding part 50 may be detached from the substrate 31.

Figure 9:
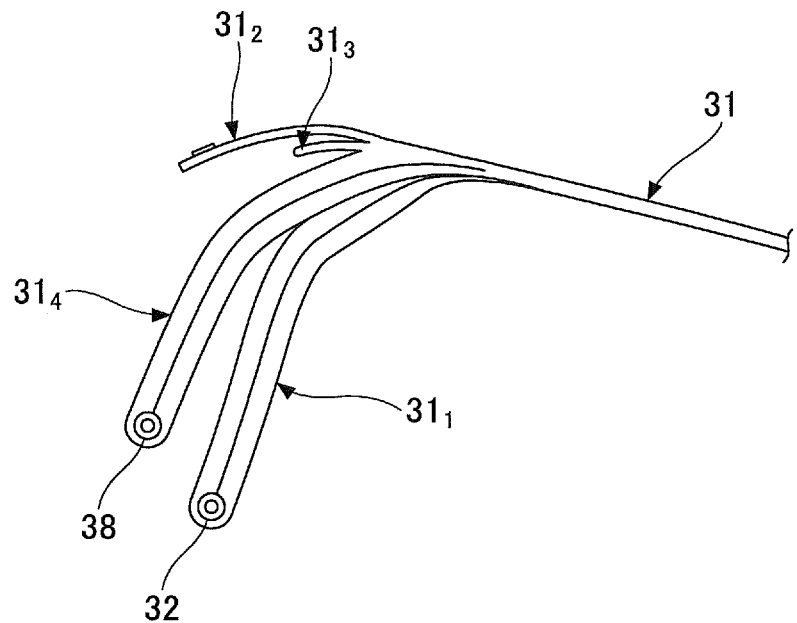
FIG. 9 is a diagram exemplifying a situation in which the marker coil according to the embodiment is curved.

Additionally, as illustrated in FIG. 9, when the marker coil unit 30 is to be attached to the head of the testee, the marker coil unit 30 can be easily attached to the head by bending (forming the shape), in advance, the coil forming parts $31_1$, $31_2$, $31_3$, and $31_4$, so that the coil forming parts $31_1$, $31_2$, $31_3$, and $31_4$ fit the shape of the head of the testee.

In order to bend, in advance, the coil forming parts $31_1$, $31_2$, $31_3$, and $31_4$, so that the coli forming parts $31_1$, $31_2$, $31_3$, and $31_4$ fit the shape of the head of the testee, thin tapes may be attached to both surface of the substrate 31. At that time, a length of the tape to be attached to a surface that is to be an inner surface when the substrate 31 is bent may be slightly shorter than a length of the tape to be attached to a surface that is to be the outer surface.

Figure 10:
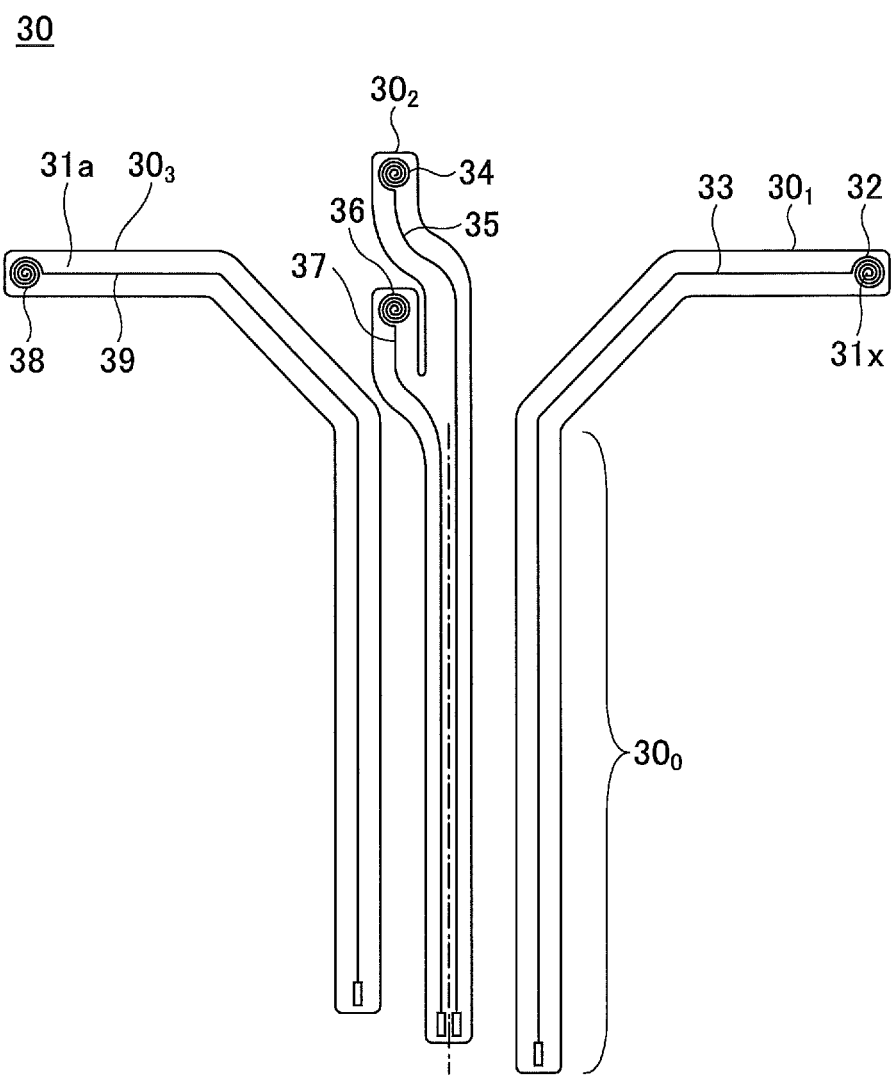
FIG. 10 is a diagram illustrating an example in which the marker coil according to the embodiment is made by combining a plurality of substrates.

In the example of FIG. 4, the marker coil unit 30 is formed of the single substrate 31. However, the marker coil unit 30 may be formed by combining a plurality of substrates. For example, as illustrated in FIG. 10, three substrates $30_1$, $30_2$, and $30_3$ may be separately formed, and the substrates $30_1$, $30_2$, and $30_3$ may be attached to each other by a double-sided tape, so that straight line parts $30_0$ of the respective substrates $30_1$, $30_2$, and $30_3$ are superposed to form the shape of FIG. 4. The number of the substrates is not limited to three. The shape of FIG. 4 may be formed by combining two substrates or four substrates.

Note that, in order to obtain the coordinate system of the magnetoencephalograph 100 in the x-direction, the y-direction, and the z-direction, it is necessary to provide three or more coils in the marker coil unit 30. In FIG. 4, the example is illustrated in which the four coils are formed in the marker coil unit 30. However, three coils or five or more coils may be formed in the marker coil unit 30. By providing four coils in the marker coil unit 30, even if one coil is detached, for example, due to sweating of the testee, the coordinate system of the magnetoencephalograph 100 in the x-direction, the y-direction, and the z-direction can be obtained by the remaining three coils.

In this manner, in the marker coil unit 30, the weight is reduced by forming the coils 32, 34, 36, and 38 by wiring in the flexible substrate 31. By forming the substrate 31 and the substrate holding parts 50 to be detachable separate bodies, the protrusions 52 of the substrate holding parts 50 can be fitted into respective holes 31x of the substrate 31 after the lightweight substrate holding parts 50 are attached to the respective predetermined parts of the head of the testee. In this manner, by attaching, in advance, the substrate holding parts 50 to the respective predetermined parts of the head of the testee, the substrate 31 can be attached to the head of the testee with four touches, so that unpleasant feeling for the testee can be mitigated, and the marker coil unit 30 can be easily attached to an infant or a little child.

Comparing the force for fitting the protrusion 52 into the hole 31x with the force for attaching the substrate holding part 50 to the head, the force for fitting the protrusion 52 into the hole 31x is weaker than the force for attaching the substrate holding part 50 to the head. Thus, when lying face up during examination, when the marker coil unit 30 is pulled, or when the marker coil unit 30 receives an impact, the substrate holding parts 50 attached to the head may remain on the head, even if the substrate holding parts 50 and the substrate 31 are detached from each other. For example, even if the testee accidentally behaves violently to remove the substrate 31 from the substrate holding parts 50, the substrate holding parts 50 remain on the head of the testee, so that the substrate 31 can be easily attached to the same position again and measurement with favorable reproducibility can be made.

The substrate holding part 50 is lightweight, so that the substrate holding part 50 can be attached to a hairy part.

Consequently, the degrees of freedom can be enhanced for the positions to which the substrate holding parts 50 are to be attached.

Furthermore, for a marker coil according to related art (e.g., the marker coil according to Patent Document 1), large force is required for removal, so that relatively heavy housing is provided so as to prevent the coils from being bent during removal. In contrast, in the marker coil unit 30, the notches 31z are formed in the substrate 31, so that the substrate 31 can be removed from the substrate holding harts 50 with force that is weaker than the force for the marker coil according to the related art. Consequently, it is not required to provide a housing, such as the housing of the related art. By only providing the reinforcing plate 41 with a simple structure, bending and distortion of the coils can be prevented, so that the weight of the entire marker coil unit 30 can be reduced.

The example the marker coil unit 30 is described above, in which the protrusions 52 of the substrate holding parts 50 are attached to and detached from (engage) the respective holes 31x formed in the substrate 31. However, it suffices, in the marker coil unit 30, to form a convex shape in one of the substrate 31 and the substrate holding part 50 and to form an engaging part that engages the convex shape in the other of the substrate 31 and the substrate holding part 50. In the following, an example is illustrated in which the convex shape is formed in the substrate 31 and the engaging part is formed in the substrate holding part 50. Note that, in the following example, a description of a component that is the same as the component of the above-described example may be omitted.

Figure 11A:
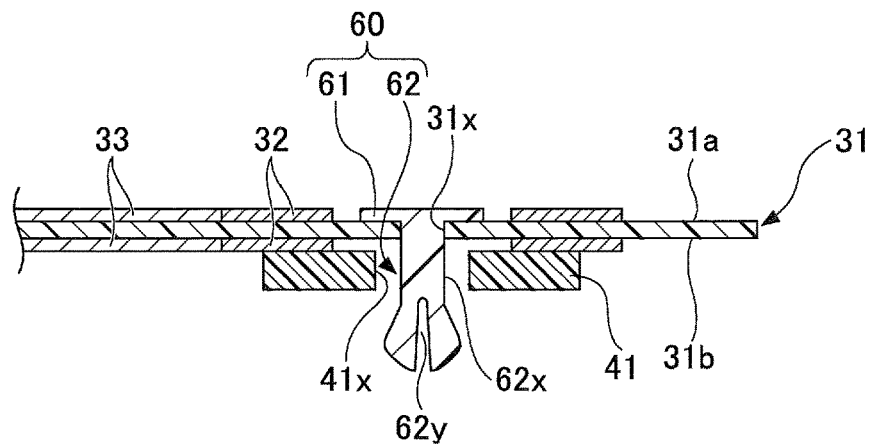
FIGS. 11A, 11B, and 11C are diagrams exemplifying a marker coil unit according to a first modified example of the embodiment.
Figure 11B:
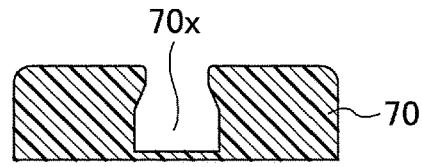
Figure 11C:
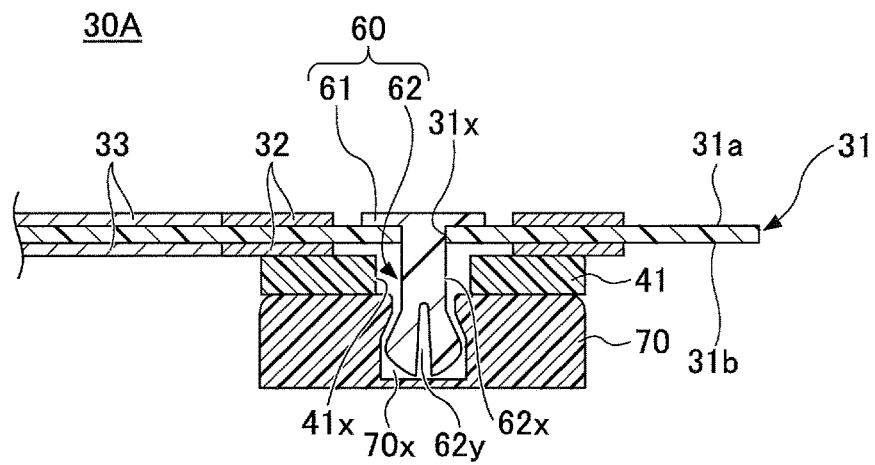

FIG. 11 is a diagram exemplifying a marker coil unit 30A according to the example. FIG. 11A is a cross-sectional view exemplifying a part of the marker coil unit 30A excluding a substrate holding part 70. FIG. 11B is a cross-sectional view exemplifying the substrate holding part 70 of the marker coil unit 30A. FIG. 11C is a cross-sectional view exemplifying a situation in which the substrate holding part 70 is attached to the substrate 31.

As illustrated in FIG. 11, the marker coil unit 30A is different from the marker coil unit 30 (cf. FIGS. 4 through 6) in the points that a convex part 60 is secured to the substrate 31 and that the substrate holding part 50 is replaced with the substrate holding part 70. Note that, in the marker coil unit 30A, the substrate holding part 70 and the other part are formed as separate bodies, and the substrate holding part 70 and the other part are integrated when the marker coil unit 30A is attached to the head of the testee.

The convex part 60 and the substrate holding part 70 may have any shape and any size, so that the convex part 60 and the substrate holding part 70 can be attached to and detached from each other. As an example, the convex part and the substrate holding part 70 may have the shapes illustrated in FIG. 11.

In FIG. 11, the convex part 60 includes a base 61 and a protrusion 62 that protrudes on one side of the base 61. The protrusion 62 of the convex part 60 is inserted into the hole 31x of the substrate 31 from a side of one surface 31a of the substrate 31, and the protrusion 62 of the convex part 60 protrudes from the other surface 31b of the substrate 31. A peripheral part of the protrusion 62 on a surface of the base 61 facing the one surface 31a of the substrate 31 is secured to the one surface 31a of the substrate 31 by an adhesive or an adhesive tape.

The convex part 60 is formed of a resin, such as acrylic. The base 61 has an approximately disk shape. However, the shape of the base 61 is not limited to this, and the base 61 may have any shape.

The substrate holding part 70 has an approximately disk shape. At the center of the substrate holding part 70, a recess 70x is formed that is the engaging part that engages the protrusion 62 of the convex part 60. The substrate holding part 70 is formed of a resin, such as acrylic.

In the protrusion 62, a narrowed part 62x is formed at a side closer to the base 61. The narrowed part 62x is the part of the protrusion 62 close to the base part 61 such that the diameter of the part is smaller than a diameter of a part of the protrusion 62 separated from the base part 61. Additionally, in the protrusion 62, a slit 62y may preferably be formed that divides the protrusion 62 into approximately two equal parts in the axis direction (the direction of the protrusion). Furthermore, the recess 70x has a shape such that the width at the side of the bottom surface is enlarged compared to the width at the side of the entrance.

The diameters of the tip and the narrowed part 62x of the protrusion 62 are adjusted to be slightly smaller than the diameter of the entrance of the recess 70x. The diameter of the thickest part of the protrusion 62, at which the slit 62y is formed, is adjusted to be slightly greater than the diameter of the entrance of the recess 70x and to be slightly smaller than the diameter of the part at the bottom surface side of the recess 70x, at which the width is enlarged.

When the tip of the protrusion 62 of the convex part 60 is contacted to the entrance of the recess 70x of the substrate holding part 70 and the convex part 60 is further pressed toward the recess 70x, the both sides of the slit 62y move inward and the protrusion 62 is fitted into the recess 70x while the slit 62y is narrowed. As the slit 62y spreads at the part of the recess 70x at which the width of the recess 70x is enlarged, the part of the protrusion 62 above the narrowed part 62x functions as a stopper, so that the protrusion 62 is not easily released from the recess 70x.

When the substrate 31 is to be removed from the substrate holding part 70, by pulling the substrate 31 in a direction in which the substrate 31 is separated from the recess 70x, the both sides of the slit 62y of the protrusion 62 move inward and the slit 62y is narrowed, so that the protrusion 62 can be easily removed from the recess 70x.

Note that, in the substrate holding part 70, instead of the recess 70x, a through hole may be formed such that the bottom part of the recess 70x is removed. In this case, the substrate 31 can be held similar to the case of the recess 70x, provided that the convex part 60 of the protrusion 62 can engage the through hole of the substrate holding part 70.

In the following, another example is described. In a part at which the substrate is attached to the substrate holding part, the convex shape and the engaging part that engages the convex shape are a part of a hook-and-loop fastener. Note that, in the following example, a description of a component that is the same as the component of the above-described example may be omitted.

Figure 12A:
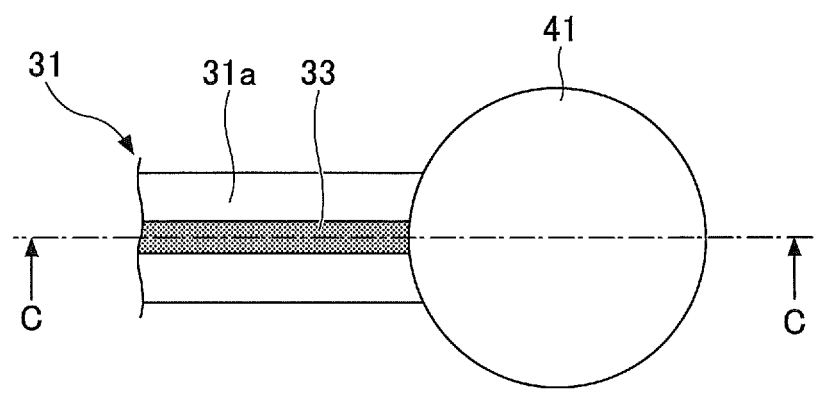
FIGS. 12A and 12B are partial enlarged views exemplifying a vicinity of a coil of the marker coil unit according a second modified example of the embodiment.
Figure 12B:
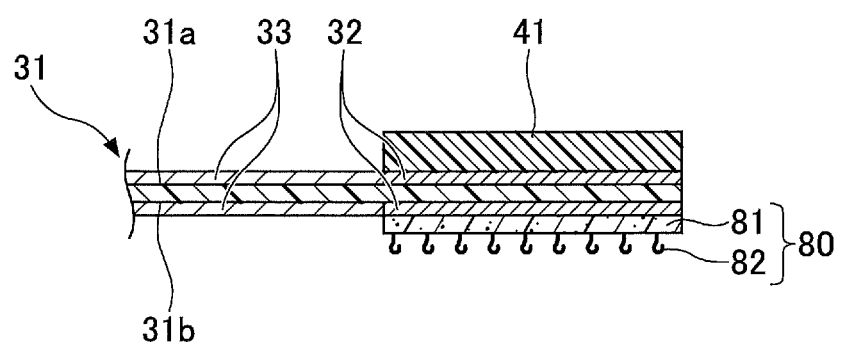
Figure 13A:
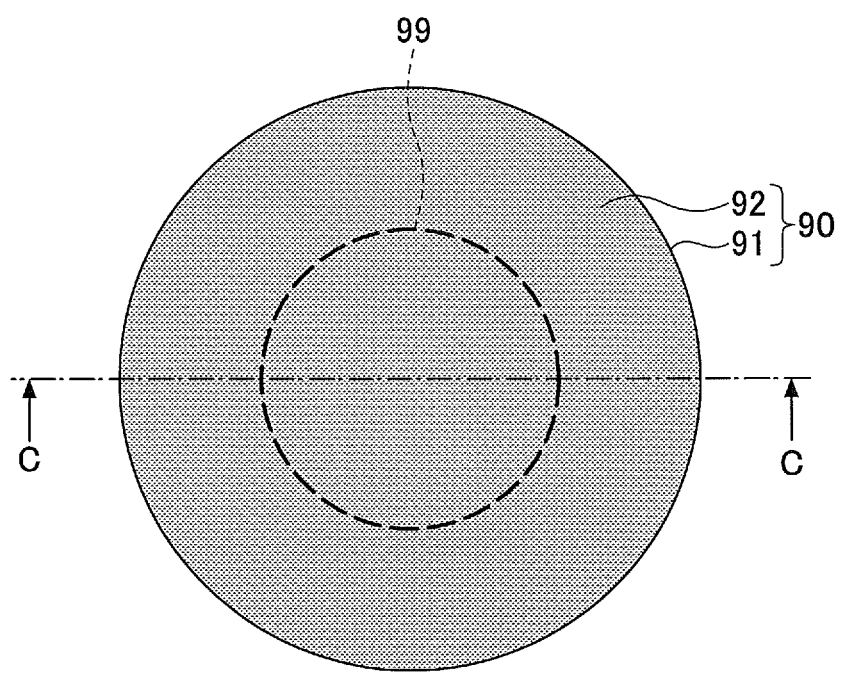
FIGS. 13A and 13B are diagrams exemplifying a substrate holding part of the marker coil unit according to the second example of the embodiment.
Figure 13B:
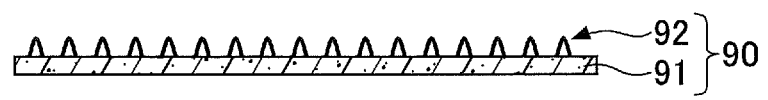
Figure 14A:
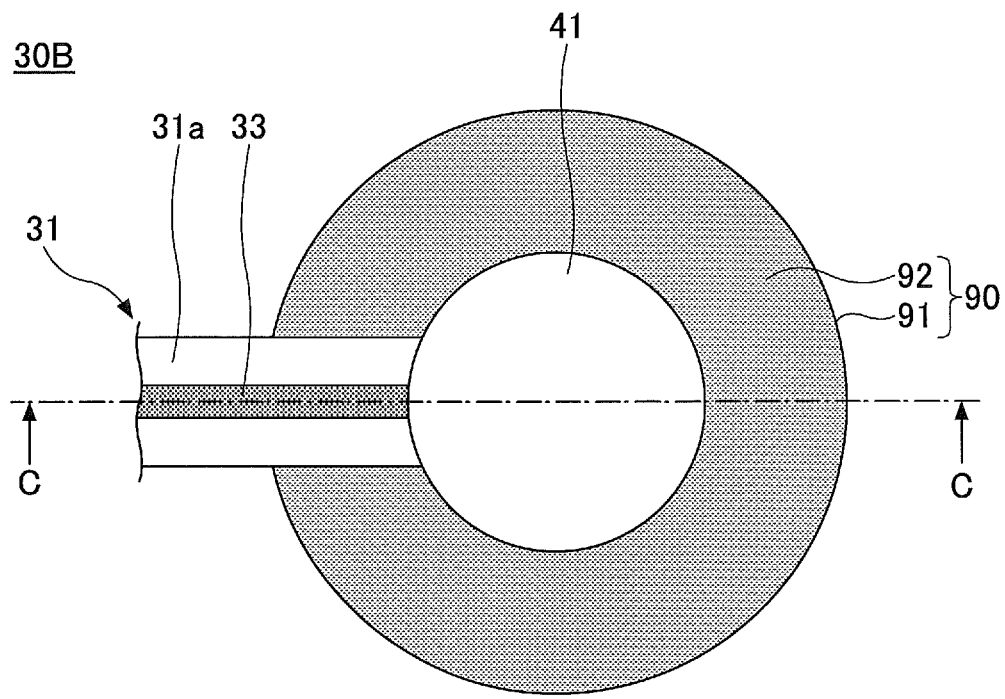
FIGS. 14A and 14B are diagrams exemplifying a situation in which the substrate holding part of the marker coil unit according to the second modified example of the embodiment is attached to the substrate.
Figure 14B:
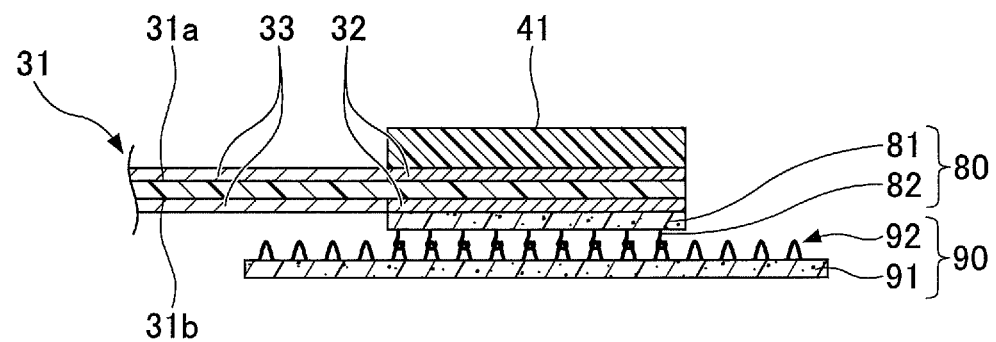

FIGS. 12A and 12B are partially enlarged views exemplifying a vicinity of a coil 32 of a marker coil unit 30B according to the example. FIGS. 13A and 13B are diagrams exemplifying a substrate holding part of the marker coil unit 30B according to the example. FIGS. 14A and 14B are diagrams exemplifying a situation in which the substrate holding part of the marker coil unit according to the example is attached to the substrate. FIG. 12A, FIG. 13A, and FIG. 14A are plan views. FIG. 12B, FIG. 13B, and FIG. 14B are cross-sectional views along the line C-C in FIG. 12A, FIG.

13A, and FIG. 14A, respectively. However, in FIG. 12B and FIG. 14B, the cross section of the coil 32 is simplified. In FIG. 12 through FIG. 14, the vicinity of the coil 32 is depicted. The vicinities of the other coils have the same structure.

As illustrated in FIGS. 12 through 14, the marker coil unit 30B includes a male hook-and-loop fastener 80 and a female hook-and-loop fastener 90, instead of the substrate holding part 50 and the hole 31x that engages the protrusion 52 of the substrate holding part 50 in the marker coil unit 30.

As illustrated in FIG. 12, in the example, the substrate 31 has a shape that corresponds to the coil 32 and the wiring 33. A reinforcing plate 41 having an approximate circular shape is secured to one side of the coil 32 arranged on one surface 31a of the substrate 31. Note that, in the example of FIG. 12, the reinforcing plate 41 is secured to the one side of the coil 32 so as to prevent the coil 32 from being bent during detachment. However, the reinforcing plates 41 may be secured to both sides of the coil 32. In this case, the same effect can be obtained.

Furthermore, the male hook-and-loop fastener 80 is provided on the other side of the coil 32 arranged on the other surface 31b of the substrate 31. The male hook-and-loop fastener 80 includes a base 81 having an approximate circular shape that is secured to the other side of the coil 32 and a plurality of hook-shaped engaging elements 82 that protrudes at the side of the base 81 other than the side at which the base 81 is secured to the other side of the coil 32. The base 81 may be formed of fibers or resins, for example. The hook-shaped engaging elements 82 may be formed of fibers, for example.

As illustrated in FIG. 13, in the example, the female hook-and-loop fastener 90 includes a base 91 having an approximate circular shape and a plurality of loop-shaped engaging elements 92 that protrudes on one side of the base 91. The female hook-and-loop fastener 90 functions as the substrate holding part. The base 91 may be formed of fibers or resins, for example. The loop-shaped engaging elements 92 may be formed of fibers, for example.

The hook-shaped engaging element 82 is a typical example of a convex shape according to the present disclosure. The loop-shaped engaging element 92 is a typical example of an engaging part that engages the convex shape according to the present disclosure. The shapes of the hook-shaped engaging element 82 and the loop-shaped engaging element 92 illustrated in FIG. 12 and FIG. 13, respectively, are merely examples. The hook-shaped engaging element 82 and the loop-shaped engaging element 92 may have any other shapes, provided that the hook-shaped engaging element 82 forms a convex shape and the loop-shaped engaging element 92 forms an engaging part that engages the convex shape.

A double-sided tape, for example, is attached to the other side of the substrate 91, so that the female hook-and-loop fastener 90 can be attached to the head of the testee. The diameter of the base 91 of the female hook-and-loop fastener 90 may preferably be greater than the diameters of the coil forming region of the substrate 31, the reinforcing plate 41, and the base 81 of the male hook-and-loop fastener 80.

On one surface of the base 91, a guide 99 that functions as a mark for attaching the base 81 is drawn to be coaxial with the base 81. The diameter of the guide 99 is almost the same as the diameter of the base 81. For example, the guide 99 may be indicated by applying a paint with a color that is different from the color of the loop-shaped engaging elements 92; by forming a circumferential space in which no loop-shape engaging element 92 is formed; or by any other method. By providing the guide 99, the coil 32 can be arranged at the predetermined position with a high precision.

After attaching the other side of the base 91 of the female hook-and-loop fastener 90 to the head of the testee, the base 81 of the male hook-and-loop fastener 80 is arranged, so that the base 81 overlaps the guide 99 of the base 91 of the female hook-and-loop fastener 90, as illustrated in FIG. 14. As a result, the loop-shaped engaging element 92 is hooked by the hook-shaped engaging element 82 to be engaged each other and the female hook-and-loop fastener 90, which is the substrate holding part, holds the substrate 31, so that each coil can be arranged at a predetermined position on the head of the testee.

Furthermore, the base 91 of the female hook-and-loop fastener 90 is formed such that the diameter of the base 91 is greater than the diameters of the coil forming region of the substrate 31, the reinforcing plate 41, and the base 81 of the male hook-and-loop fastener 80. Thus, when the substrate 31 is to be removed from the head of the testee, the substrate 31 can be easily removed by pressing the outer peripheral part of the base 91.

In the marker coil unit 30, the protrusion 52 of the substrate holding part 50 is fitted into the hole 31x of the substrate 31 to be engaged. The marker coil is attached to a position close to the ear, so that a discomfortable cracking sound may be heard during the attachment of the substrate 31 to the substrate holding parts 50. An infant or a little child may dislike this sound.

In the marker coil unit 30B, the loop-shaped engaging element 92 is hooked by the hook-shaped engaging element 82 to be engaged. In this case, during the attachment of the marker coil unit 30B, the discomfortable sound is not generated, so that the above-described problem can be resolved.

In the structure in which the loop-shaped engaging element 92 is hooked by the hook-shaped engaging element 82 to be engaged, unlike the case of the marker coil unit 30, it is not necessary to form the hole 31x in the substrate 31 positioned at the center of the coil. In order to identify the center of the coil, the coil may preferably be wound so that the coil approaches the center as much as possible. In the marker coil unit 30B, the coil can be wound in the region in which the hole 31x would be formed, if it were the marker coil unit 30, so that the precision for identifying the center of the coil can be enhanced.

In the marker coil unit 30B, the loop-shaped engaging element 92 is more flexible (softer) than the hook-shaped engaging element 82. In the marker coil unit 30B, the flexible loop-shaped engaging elements 92 are arranged on the head of the testee, so that, when the loop-shaped engaging elements 92 are attached to the head of the testee, it is unlikely that hairs are caught by the loop-shaped engaging elements 92 to cause pain for the testee.

Figure 15A:
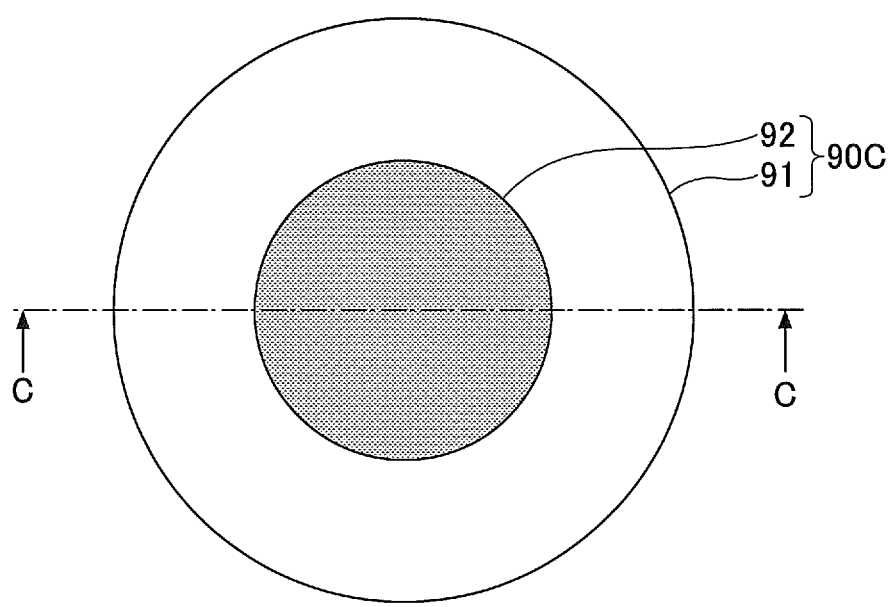
FIGS. 15A and 15B are diagrams (version 1) illustrating another example of the substrate holding part.
Figure 15B:
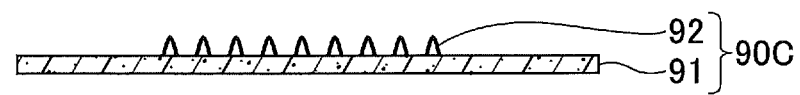

As in a female hook-and-loop fastener 90C illustrated in FIGS. 15A and 15B, the loop-shaped engaging elements 92 may be provided on one side of the base 91 only in the region in which the male hook-and-loop fastener 80 is to be attached. In this case, the loop-shaped engaging elements 92 themselves function as a guide, so that it is not necessary to form the guide 99.

Figure 16A:
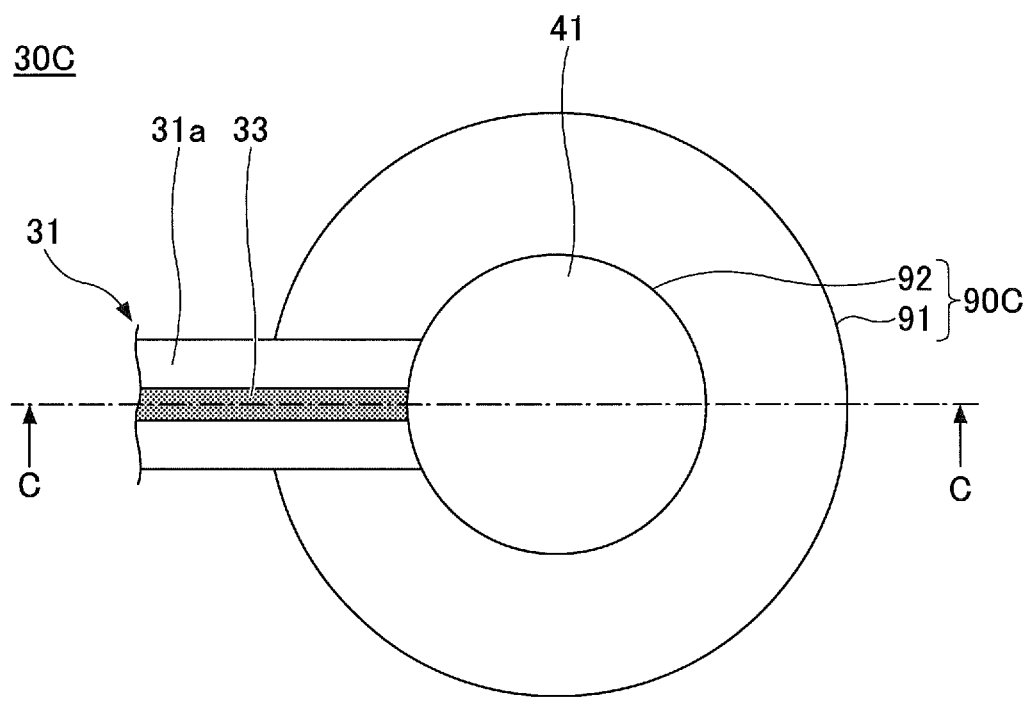
FIGS. 16A and 16B are diagrams (version 2) illustrating another example of the substrate holding part.
Figure 16B:
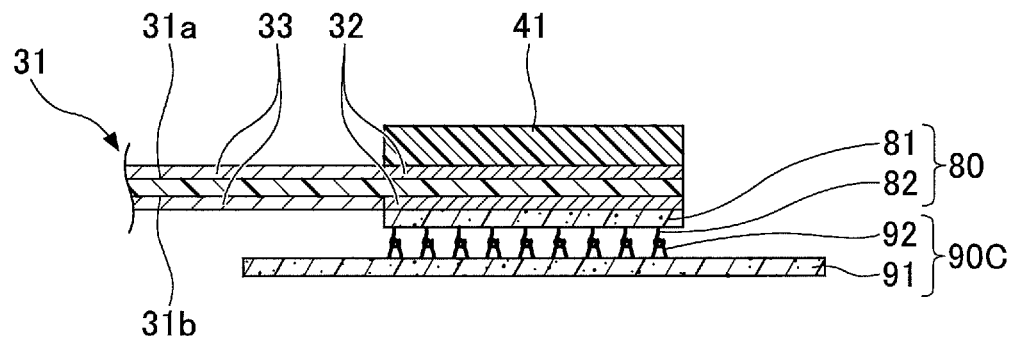

After attaching the other side of the base 91 of the female hook-and-loop fastener 90C to the head of the testee, the base 81 of the male hook-and-loop fastener 80 is arranged, so that the base 81 overlaps the loop-shaped engaging elements 92 of the female hook-and-loop fastener 90C, as shown in FIG. 16B. As a result, the loop-shaped engaging elements 92 are hooked by the hook-shaped engaging elements 82 to be engaged, so that the female hook-and-loop fastener 90C, which is the substrate holding part, holds the substrate 31 and each coil can be arranged at a predetermined position on the head of the testee.

In the following, another example is described. In the part at which the substrate is attached to the substrate holding part, the convex shape and the engaging part that engages the convex shape are a part of a hook-and-loop fastener. Note that, in the following example, a description of a component that is the same as the component of the above-described example may be omitted.

Figure 17A:
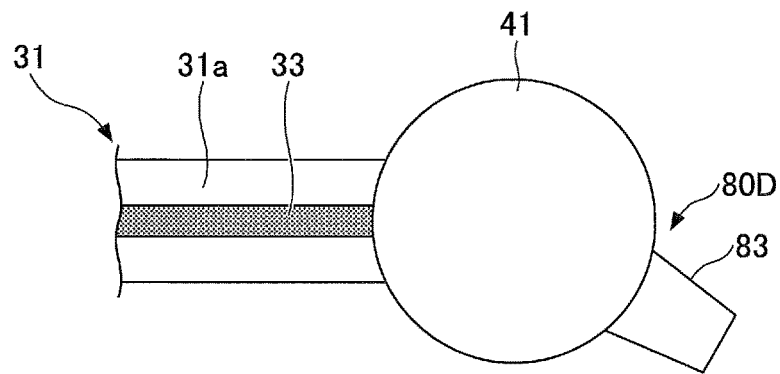
FIGS. 17A through 17C are diagrams illustrating a marker coil unit according to a third modified example of the embodiment.
Figure 17B:
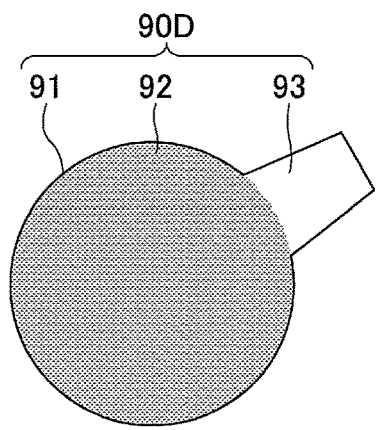
Figure 17C:
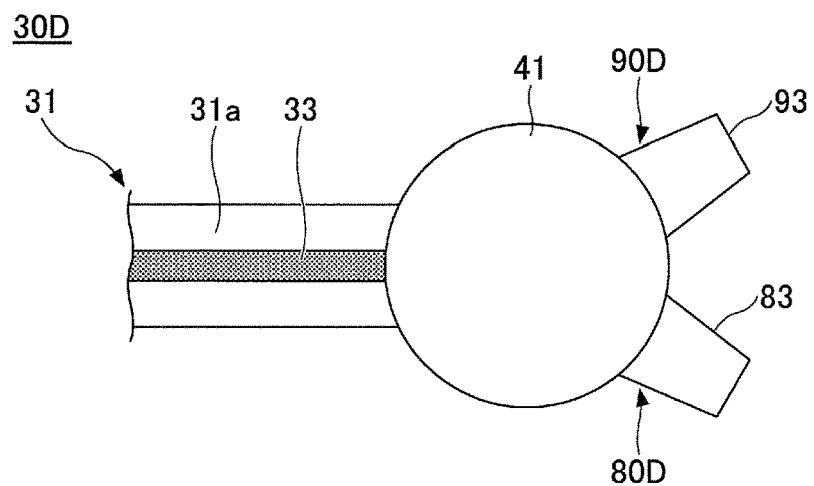

FIGS. 17A, 17B, and 17C are diagrams illustrating a marker coil unit 30D according to the example. FIG. 17A is a plan view exemplifying a vicinity of a coil of the marker coil unit 30D. FIG. 17B is a plan view exemplifying a substrate holding part 50 of the marker coil unit 30D. FIG. 17C is a plan view exemplifying a situation in which the substrate holding part 50 of the marker coil unit 30D is attached to the substrate 31.

As illustrated in FIGS. 17A, 17B, and 17C, the marker coil unit 30D includes a male hook-and-loop fastener 80D and a female hook-and-loop fastener 90D, instead of the substrate holding part 50 and the hole 31x that engages the protrusion 52 of the substrate holding part 50 of the marker coil unit 30.

As illustrated in FIG. 17A, the male hook-and-loop fastener 80D according to the example is different from the male hook-and-loop fastener 80 (cf. FIG. 12) in a point that an extension part 83 is formed in the male hook-and-loop fastener 80D. Here, the extension part 83 extends outward from a part of the outer edge of the base 81 having an approximate circular shape. The cross-sectional structure in the vicinity of the coil is the same as the structure illustrated in FIG. 12B. Note that the hook-shaped engaging elements 82 are not formed in the extension part 83.

As illustrated in FIG. 17B, the female hook-and-look fastener 90D is different from the female hook-and-loop fastener 90 (cf. FIG. 13) in a point that the diameter of the base 91 having an approximate circular shape is almost the same as the diameter of the base 81; in a point that an extension part 93 is formed that extends outward from a part of the outer edge of the base 91; and in a point that the guide 99 is not formed. The cross-sectional structure of the female hook-and-loop fastener 90D is the same as the cross-sectional structure illustrated in FIG. 13B. Note that the loop-shaped engaging elements 92 may be formed in the extension part 93.

After attaching the other side of the base 91 of the female hook-and-loop fastener 90D to the head of the testee, the base 81 of the male hook-and-loop fastener 80D is arranged, so that the base 81 overlaps the base 91 of the female hook-and-loop fastener 90D, as illustrated in FIG. 17C. As a result, the loop-shaped engaging element 92 is hooked by the hook-shaped engaging element 82 to be engaged and the female hook-and-loop fastener 90D, which is the substrate holding part, holds the substrate 31, so that each coil can be arranged at a predetermined position on the head of the testee.

As illustrated in FIG. 17C, in the marker coil unit 30D, the extension part 83 and the extension part 93 are formed such that the extension part 83 and the extension part 93 do not overlap each other in the plan view. Thus, when the substrate 31 is to be removed from the head of the testee, the substrate 31 can be easily removed by pulling the extension part 83 while holding the extension part 93.

The effect obtained by the structure such that the loop-shaped engaging element 92 is hooked by the hook-shaped engaging element 82 to be engaged is the same as the effect of the marker coil unit 30B.

In the following, another example is described. In the part at which the substrate is attached to the substrate holding part, the convex shape and the engaging part that engages the convex shape are a part of a hook-and-loop fastener. Note that, in the following example, a description of a component that is the same as the component of the above-described example may be omitted.

Figure 18A:
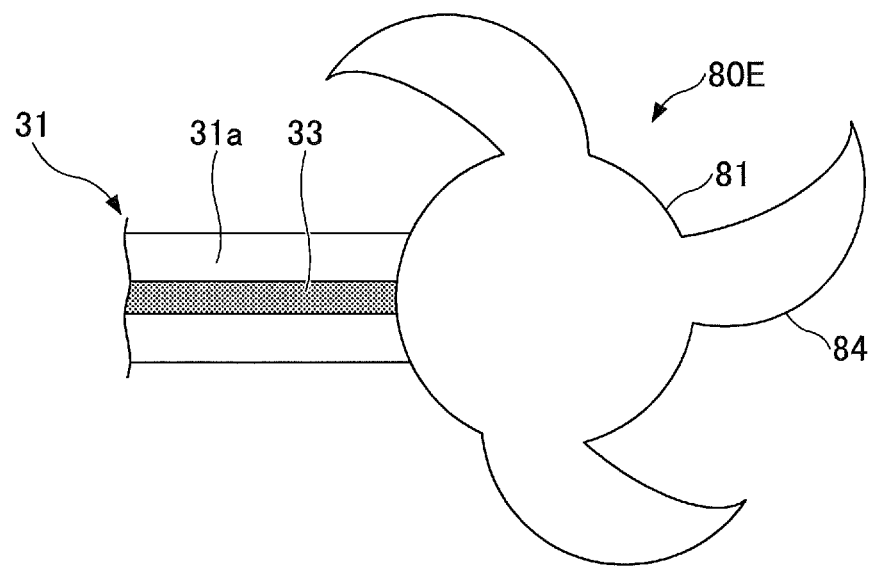
FIGS. 18A and 18B are diagrams (version 1) illustrating a marker coil unit according to a fourth modified example of the embodiment.
Figure 18B:
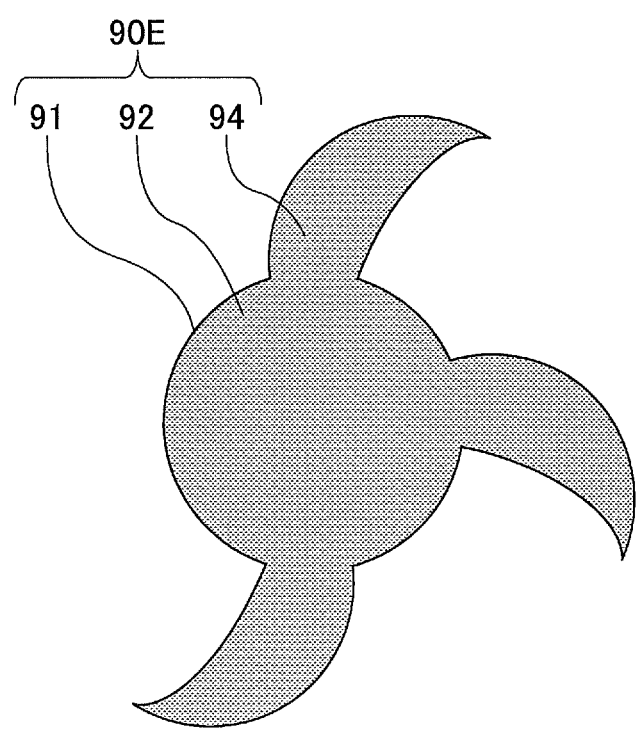
Figure 19A:
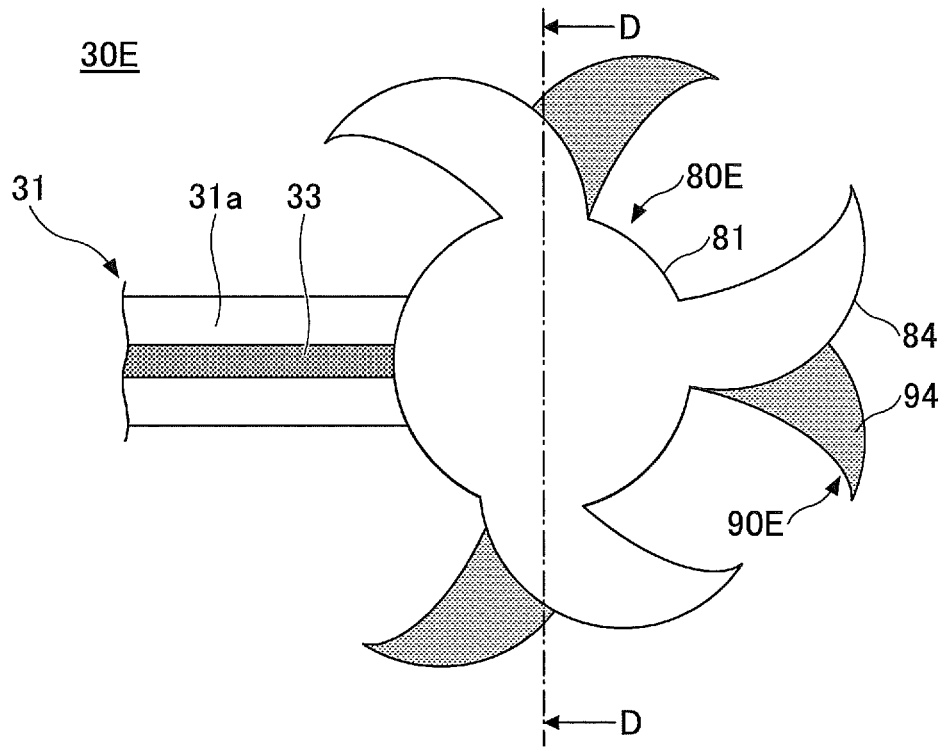
FIGS. 19A and 19B are diagrams (version 2) illustrating a marker coil unit according to the fourth modified example of the embodiment.
Figure 19B:
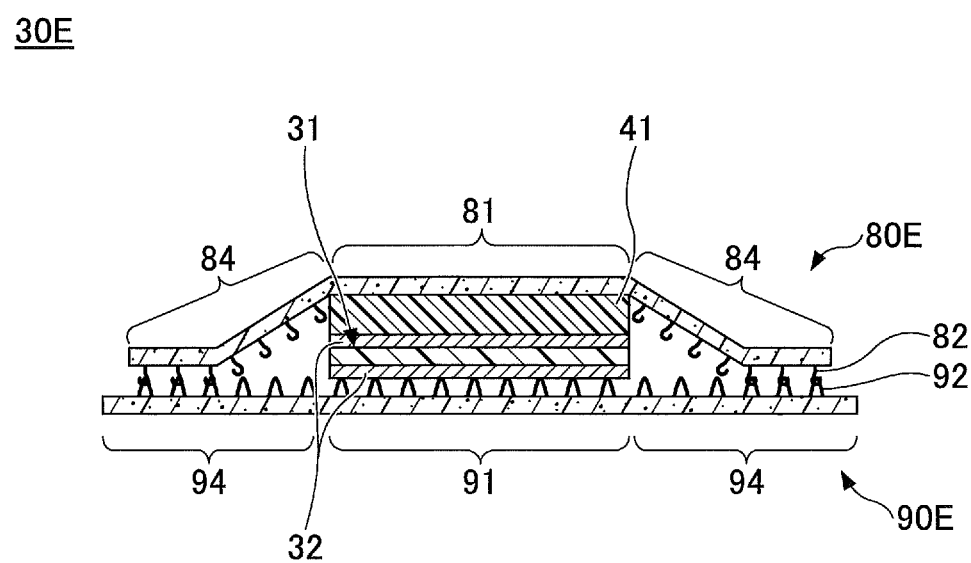

FIGS. 18A and 18B are diagrams (version 1) illustrating a marker coil unit 30E according to the example. FIG. 18A is a plan view exemplifying a vicinity of a coil of the marker coil unit 30E. FIG. 18B is a plan view exemplifying a substrate holding part of the marker coil unit 30E. FIGS. 19A and 19B are diagrams (version 2) illustrating the marker coil unit 30E according to the example. FIG. 19A is a plane view. FIG. 19B is a cross-sectional view along the line D-D in FIG. 19A.

As illustrated in FIG. 18 and FIG. 19, the marker coil unit 30E includes a male hook-and-loop fastener 80E and a female hook-and-loop fastener 90E, instead of the substrate holding part 50 and the hole 31x that engages the protrusion 50 of the substrate holding part 50 in the marker coil unit 30.

As illustrated in FIG. 18A, in the male hook-and-loop fastener 80E according to the example, three extension parts 84 are formed. Each of the three extension parts 84 extends outward from a part of an outer edge of a base 81 having an approximate circular shape. Each of the three extension parts 84 has an approximate crescent shape. Furthermore, as illustrated in FIG. 19B, in the male hook-and-loop fastener 80E, a reinforcing plate 41 is secured to the other side of the base 81. On the other side of the reinforcing plate 41, the coil 32 formed on the substrate 31 is secured. On the other side of the extension part 84, the hook-shaped engaging elements 82 are formed.

As illustrated in FIG. 18B, in the female hook-and-loop fastener 90E according to the example, three extension parts 94 are formed. Each of the three extension parts 94 extends outward from a part of an outer edge of a base 91 having an approximate circular shape. Here, the diameter of the base 91 is almost the same as the diameter of the base 81. Each of the three extension parts 94 has an approximate crescent shape. On one side of the base 91 and the extension parts 94, the loop-shaped engaging elements 92 are formed. The cross-sectional structure of the female hook-and-loop fastener 90E is as illustrated in FIG. 19B.

After attaching the other side of the base 91 of the female hook-and-loop fastener 90E to the head of the testee, the base 81 of the male hook-and-loop fastener 80E is arranged, so that a part of each extension part 84 close to the base 81 overlaps a part of the corresponding extension part 94 close to the base 91 in the plan view, as illustrated in FIG. 19A and FIG. 19B.

As a result, in a part where the extension part 84 overlaps the extension part 94 in the plan view, the loop-shaped engaging element 92 is hooked by the hook-shaped engaging element 82 to be engaged and the female hook-and-loop fastener 90E, which is the substrate holding part, holds the substrate 31, so that each coil can be arranged at a predetermined position on the head of the testee.

The tip side of the extension part 84 is shifted from the tip side of the extension part 94. In other words, the tip side of the extension part 84 does not overlap the tip side of the extension part 94 in the plan view. Thus, when the substrate 31 is to be removed from the head of the testee, the substrate 31 can be easily removed by pulling the extension part 84, while holding the extension part 94.

The effect obtained by the structure such that the loop-shaped engaging element 92 is hooked by the hook-shaped engaging element 82 to be engaged is the same as the effect of the marker coil unit 30B.

Note that, if there are at least two pairs of the extension part 84 and the extension part 94, the female hook-and-loop fastener 90E, which is the substrate holding part, can hold the substrate 31. If there are three or more pairs of the extension part 84 and the extension part 94, the female hook-and-loop fastener 90E, which is the substrate holding part, can more stably hold the substrate 31.

In the following, another example is described. In the part at which the substrate is attached to the substrate holding part, the convex shape and the engaging part that engages the convex shape are a part of a hook-and-loop fastener. Note that, in the following example, a description of a component that is the same as the component of the above-described example may be omitted.

Figure 20A:
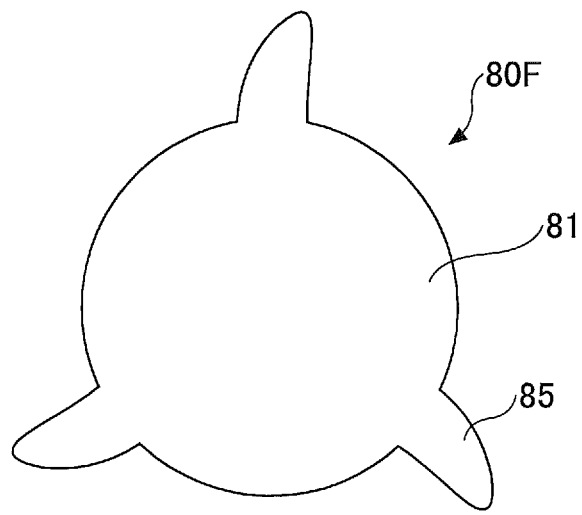
FIGS. 20A and 20B are diagrams (version 1) illustrating a marker coil unit according to a fifth modified example of the embodiment.
Figure 20B:
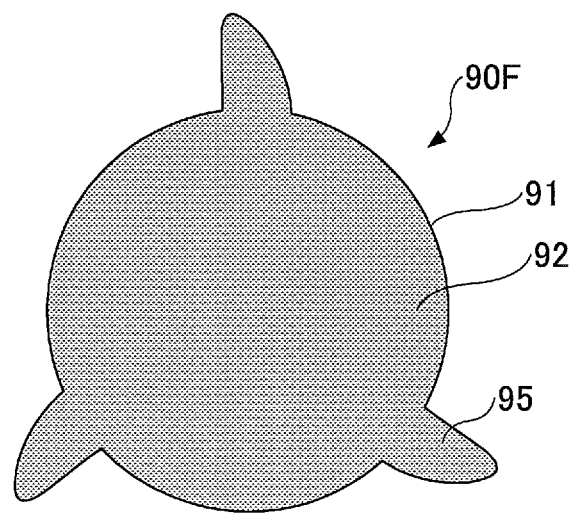
Figure 21A:
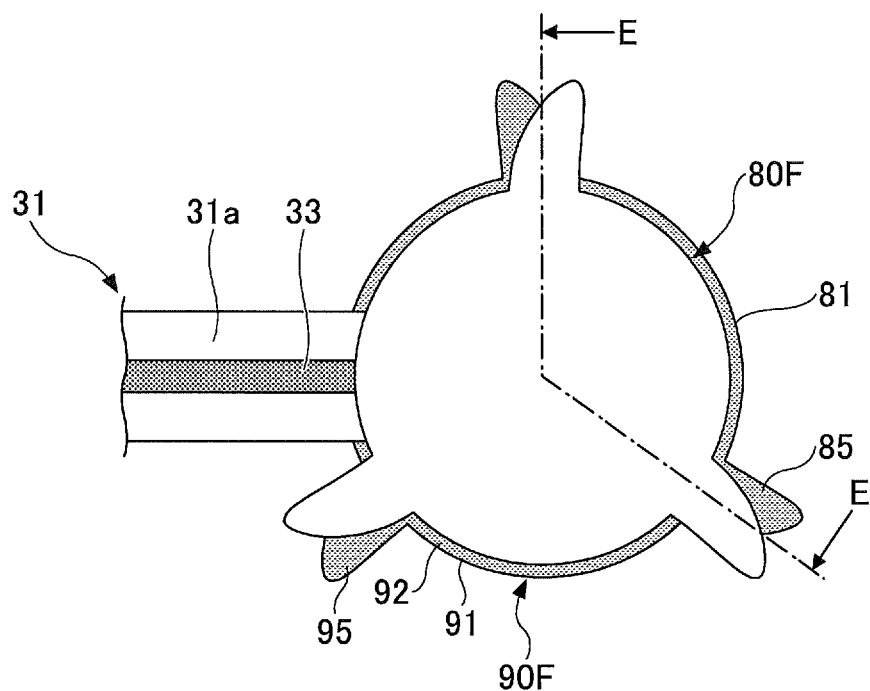
FIGS. 21A and 21B are diagrams (version 2) illustrating a marker coil unit according to the fifth modified example of the embodiment.
Figure 21B:
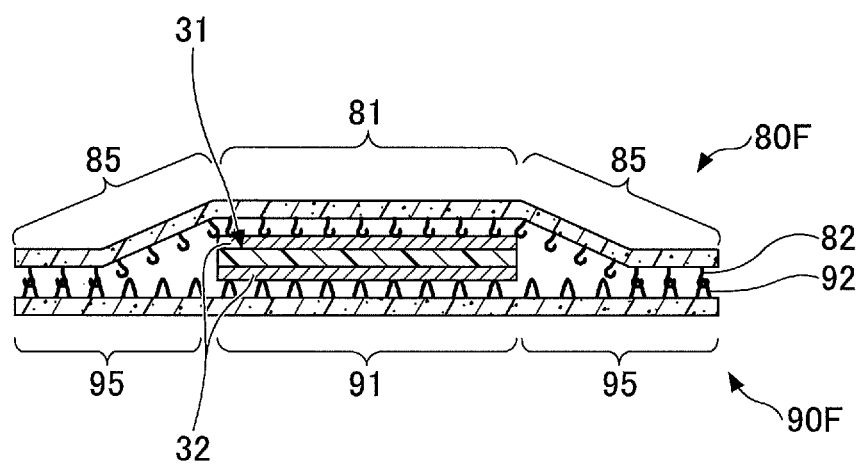

FIGS. 20A and 20B are diagrams (version 1) illustrating a marker coil unit 30F according to the example. FIG. 20A is a plan view exemplifying a vicinity of a coil of the marker coil unit 30F. FIG. 20B is a plan view exemplifying a substrate holding part of the marker coil unit 30F. FIGS. 21A and 21B are diagrams (version 2) illustrating the marker coil unit 30F according to the example. FIG. 21A is a plane view. FIG. 21B is a cross-sectional view along the line E-E in FIG. 21A.

As illustrated in FIG. 20 and FIG. 21, the marker coil unit 30F includes a male hook-and-loop fastener 80F and a female hook-and-loop fastener 90F, instead of the substrate holding part 50 and the hole 31x that engages the protrusion 50 of the substrate holding part 50 in the marker coil unit 30. The male hook-and-loop fastener 80F and the female hook-and-loop fastener 90F are not integrally formed with the substrate 31 and the coil 32.

As illustrated in FIG. 20A, the male hook-and-loop fastener 80F according to the example includes a base 81 having an approximate circular shape and three extension parts 85. Each of the three extension parts 85 extends outward from a part of an outer edge of the base 81. The three extension parts 85 are almost evenly spaced. Namely, a central angle formed by the adjacent extension parts 85 is approximately 120 degrees.

One edge of the extension part 85 along the longitudinal direction has an approximate linear shape, and the other edge of the extension part 85 along the longitudinal direction has an approximate knife shape that is curved. Furthermore, as illustrated in FIG. 21B, in the male hook-and-loop fastener 80F, the hook-shaped engaging elements 82 are formed on the other side of the base 81 and the extension part 85.

As illustrated in FIG. 20B, the female hook-and-loop fastener 90F according to the example includes a base 91 having an approximate circular shape and three extension parts 95. The diameter of the base 91 is almost the same as the diameter of the base 81. Each of the three extension parts 95 extends outward from a part of an outer edge of the base 91. The three extension parts 95 are almost evenly spaced. Namely, a central angle formed by the adjacent extension parts 95 is approximately 120 degrees.

One edge of the extension part 95 along the longitudinal direction has an approximate linear shape, and the other edge of the extension part 95 along the longitudinal direction has an approximate knife shape that is curved. However, the extension part 85 and the extension part 95 are formed to have shapes that are approximately line symmetrical with respect to the center line in the longitudinal direction. Furthermore, as illustrated in FIG. 21B, in the female hook-and-loop fastener 90F, the loop-shaped engaging elements 92 are formed on the other side of the base 91 and the extension part 95.

After attaching the other side of the base 91 of the female hook-and-loop fastener 90F to the head of the testee, the substrate 31 on which the coil 32 is formed is arranged, as illustrated in FIG. 21A and FIG. 21B, and the base 81 of the male hook-and-loop fastener 80F is arranged, so that a part of each extension part 85 close to the base 81 overlaps a part of the corresponding extension part 95 close to the base 91.

As a result, in a part where the extension part 85 overlaps the extension part 95 in the plan view, the loop-shaped engaging element 92 is hooked by the hook-shaped engaging element 82 to be engaged and the female hook-and-loop fastener 90F, which is the substrate holding part, holds the substrate 31, so that each coil can be arranged at a predetermined position on the head of the testee.

The tip side of the extension part 85 is shifted from the tip side of the extension part 95. In other words, the tip side of the extension part 85 does not overlap the tip side of the extension part 95 in the plan view. Thus, when the substrate 31 is to be removed from the head of the testee, the substrate 31 can be easily removed by pulling the extension part 85, while holding the extension part 95.

The effect obtained by the structure such that the loop-shaped engaging element 92 is hooked by the hook-shaped engaging element 82 to be engaged is the same as the effect of the marker coil unit 30B.

If there are three or more pairs of the extension part 85 and the extension part 95, the female hook-and-loop fastener 90F, which is the substrate holding part, can more stably hold the substrate 31.

In the following, further examples are described. In the part at which the substrate is attached to the substrate holding part, the convex shape and the engaging part that engages the convex shape are a part of a hook-and-loop fastener. Note that, in the following examples, a description of a component that is the same as the component of the above-described example may be omitted.

Figure 22:
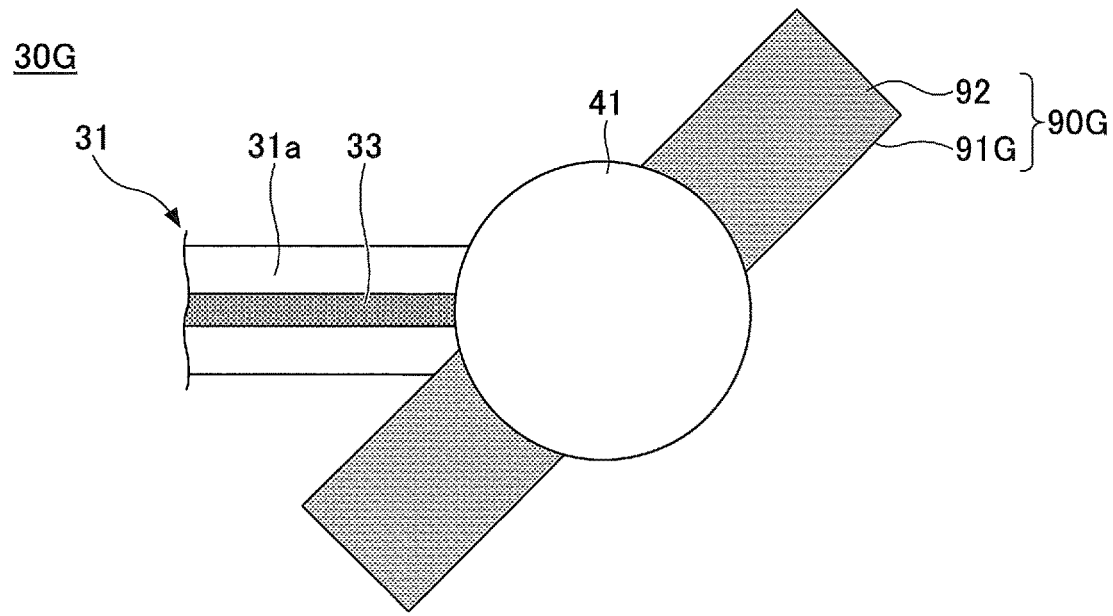
FIG. 22 is a diagram exemplifying a situation in which a substrate holding part of a marker coil unit according to a sixth modified example of the embodiment is attached to the substrate.

FIG. 22 is a diagram exemplifying a situation in which a substrate holding part of a marker coil unit 30G according to one of the examples is attached to the substrate 31.

As illustrated in FIG. 22, the marker coil unit 30G is different from the marker coil unit 30B (cf. FIGS. 12 through 14) in a point that the female hook-and-loop fastener 90 is replaced with a female hook-and-loop fastener 90G. The structure of the male hook-and-loop fastener 80 and the cross-sectional structure when the male hook-and-loop fastener 80 is attached to the female hook-and-loop fastener 90G are the same as the structure and the cross-sectional structure illustrated in FIG. 12 and FIG. 14.

As illustrated in FIG. 22, the shape of the female hook-and-loop fastener 90G may be different from the shape of the coil and the shape of the male hook-and-loop fastener 80. In the female hook-and-loop fastener 90G illustrated in FIG. 22, a base 91G is formed to have a ribbon shape (elongated rectangular shape). When the base 91 has the ribbon shape (the elongated rectangular shape), an effect is obtained such that, by attaching the base 91 along a parting of the hair, a bonding area on the scalp can be enlarged.

The base 91G may have a cross shape. When the base 91 has the cross shape, an effect is obtained such that the position to which the male-hook- and loop fastener 80 is to be attached (the center position of the cross) can be easily found.

Figure 23:
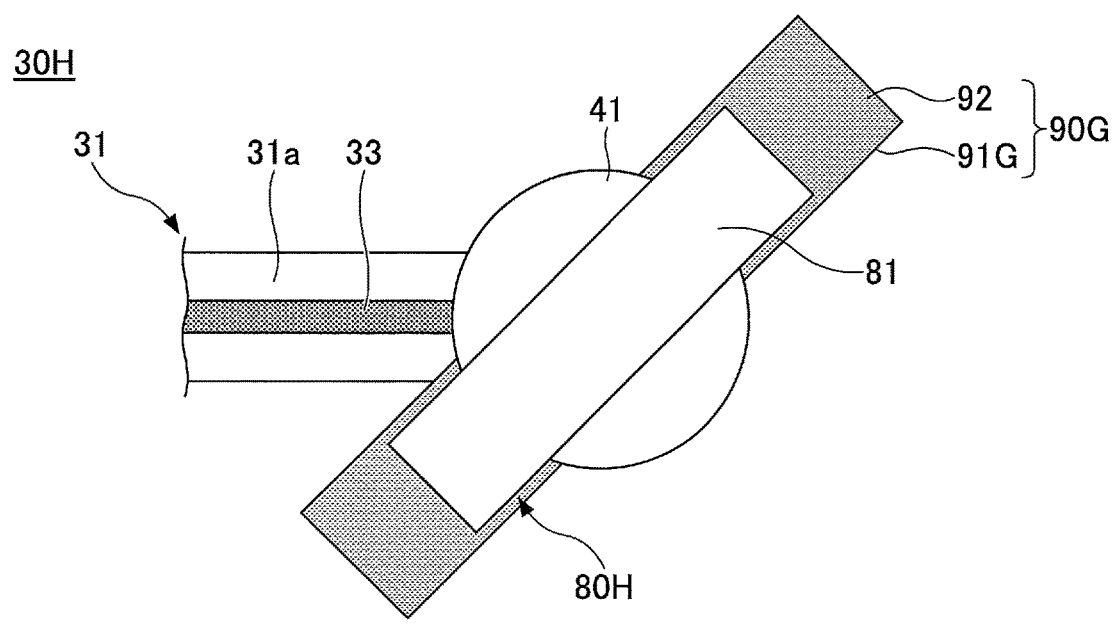
FIG. 23 is a diagram exemplifying a situation in which a substrate holding part of a marker coil unit according to a seventh modified example of the embodiment is attached to the substrate.

FIG. 23 is a diagram exemplifying a situation in which a substrate holding part of a marker coil unit 30H according to the other one of the examples is attached to the substrate 31.

As illustrated in FIG. 23, the marker coil unit 30H is different from the marker coil unit 30G (cf. FIG. 22) in a point that the male hook-and-loop fastener 80 is replaced with a male hook-and-loop fastener 80H. The cross-sectional structure of the male hook-and-loop fastener 80H and the cross-sectional structure when the male hook-and-loop fastener 80H is attached to the female hook-and-loop fastener 90G are the same as the cross-sectional structure illustrated in FIG. 19B.

In the male hook-and-loop fastener 80H illustrated in FIG. 23, a base 81 is formed to have a ribbon shape (elongated rectangular shape). As described above, the shape of the male hook-and-loop fastener 80H may be different from the shape of the coil.

The preferred embodiments are described in detail above. However, the present invention is not limited to the above-described embodiments, and various modifications and substitutions may be made to the above-described embodiments without departing from the scope described in the claims.

In the above-described embodiments, the example is described such that, in the marker coil unit 30, the hole 31x is formed at the center of the coil formed on the substrate 31. The hole 31x is for attaching and detaching the protrusion 52 of the substrate holding part 50. If the hole 31x is formed at the center of the coil formed on the substrate 31, the coil is not easily shifted and the coil is not easily bent, even if the testee moves. Thus, it is preferable to form the hole 31x at the center of the coil formed on the substrate 31. Furthermore, in order to enhance the alignment accuracy with respect to a MRI image, a three-dimensional coordinates of the marker coil unit 30 may be obtained by using a 3D digitizer. In this case, by forming the hole 31x at the center of the coil formed on the substrate 31, the calculation for obtaining the three-dimensional coordinates can be simplified. However, the substrate holding part 50 is for holding the substrate 31, so that it is not necessary to form the hole 31x at the center of the coil formed on the substrate 31. The hole 31x may be formed at a desired position on the substrate 31.

Furthermore, in the above-described embodiment, an example is described in which the marker coil unit according to the present disclosure is used for a magnetoencephalograph. However, the marker coil unit according to the present disclosure may be used for a biomagnetism measurement meter other than the magnetoencephalograph (e.g., a magnetospinography). At this time, the marker coil unit according to any one of the embodiments can be easily attached to a part of the body (a body, an arm, etc.) of the testee other than the head.

The present invention is not limited to the specifically disclosed embodiments, and variations and modifications may be made without departing from the scope of the present invention.

The present application is based on and claims the benefit of priority of Japanese priority application No. 2016-113339 filed on Jun. 7, 2016, and Japanese priority application No. 2017-085161 filed on Apr. 24, 2017, the entire contents of which are hereby incorporated herein by reference.

What is claimed is:

1. A marker coil comprising:
   a substrate;
   a first conductor line formed on a first surface of the substrate and a second conductor line formed on a second surface of the substrate;
   a coil formed on the first surface of the substrate and the second surface of the substrate by a conductor line coupled to the first conductor line and the second conductor line;
   a substrate holding part that is capable of being attached to a testee,
   wherein the coil includes a first spiral pattern on the first surface and a second spiral pattern on the second surface,
   wherein the first conductor line on the first surface is parallel to the second conductor line on the second surface,
   wherein a convex shape is formed in the substrate, and a hole for engaging the convex shape is formed in the substrate holding part, and
   wherein, upon supplying an electric current to the coil through the first conductor line and the second conductor line, electric currents in identical directions flow in the first spiral pattern and the second spiral pattern, respectively, and electric currents in opposite directions flow in the first conductor line and the second conductor line, respectively.

2. The marker coil according to claim 1, wherein the convex shape is formed at a center of the coil.

3. The marker coil according to claim 1, wherein the convex shape has a narrowed part for fitting the hole.

4. The marker coil according to claim 1, wherein a notch is formed around the hole, the notch extending outward from an outer edge of the hole.

5. The marker coil according to claim 1, wherein a reinforcing plate is formed on the coil formed on the substrate.

6. The marker coil according to claim 1, wherein the substrate includes a common part and a plurality of coil forming parts, the plurality of coil forming parts being branched from the common part,
   wherein, in each of the plurality of coil forming parts, the coil is formed.

7. The marker coil according to claim 1, further comprising:
   an electric current input part configured to input the electric current to the coil,
   wherein the electric current input part includes a connector formed on the substrate, and the first conductor line and the second conductor line for coupling a terminal of the connector to the coil.

8. A marker coil comprising:
   a substrate;
   a plurality of coil units formed on the substrate; and
   a substrate holding part that is capable of being attached to a testee,
   wherein each of the coil units includes
      a first conductor line formed on a first surface of the substrate and a second conductor line formed on a second surface of the substrate; and
      a coil formed on the first surface of the substrate and the second surface of the substrate by a conductor line coupled to the first conductor line and the second conductor line,
   wherein the coil includes a first spiral pattern on the first surface and a second spiral pattern on the second surface, wherein the first conductor line on the first surface is parallel to the second conductor line on the second surface, wherein a convex shape is formed in the substrate, and a hole for engaging the convex shape is formed in the substrate holding part, wherein, upon supplying an electric current to the coil through the first conductor line and the second conductor line, electric currents in identical directions flow in the first spiral pattern and the second spiral pattern, respectively, and electric currents in opposite directions flow in the first conductor line and the second conductor line, respectively, and wherein the marker coil is capable of being attached to a part of a body of the testee in a headband shape.

9. The marker coil according to claim 8, wherein the substrate is provided with an anti-slip sheet for covering the plurality of coil units.

10. The marker coil according to claim 8, wherein a reinforcing plate is formed on each of the coil units formed on the substrate.

11. A marker coil unit comprising:

a marker coil including a substrate, a plurality of coil units formed on the substrate, and a substrate holding part that is capable of being attached to a testee, wherein the marker coil is capable of being attached to a part of a body of the testee in a headband shape, wherein each of the plurality of coil units includes a first conductor line formed on a first surface of the substrate and a second conductor line formed on a second surface of the substrate; and a coil formed on the first surface of the substrate and the second surface of the substrate by a conductor line coupled to the first conductor line and the second conductor line, wherein the coil includes a first spiral pattern on the first surface and a second spiral pattern on the second surface, wherein the first conductor line on the first surface is parallel to the second conductor line on the second surface, wherein a convex shape is formed in the substrate, and a hole for engaging the convex shape is formed in the substrate holding part, and wherein, upon supplying an electric current to the coil through the first conductor line and the second conductor line, electric currents in identical directions flow in the first spiral pattern and the second spiral pattern, respectively, and electric currents in opposite directions flow in the first conductor line and the second conductor line, respectively; and an electric current input part configured to input electric currents to the respective coil units, wherein the electric current input part includes connectors formed on the substrate for coupling the electric current input part to the respective coil units.

* * * * *